US010117907B2

(12) United States Patent
Polt et al.

(10) Patent No.: US 10,117,907 B2
(45) Date of Patent: Nov. 6, 2018

(54) GLYCOSYLATED PACAP/VIP ANALOGUES WITH ENHANCED CNS PENETRATION FOR TREATMENT OF NEURODEGENERATIVE DISEASES

(71) Applicant: THE ARIZONA BOARD OF REGENTS ON BEHALF OF THE UNIVERSITY OF ARIZONA, Tucson, AZ (US)

(72) Inventors: Robin Polt, Tucson, AZ (US); Torsten A E Falk, Tucson, AZ (US)

(73) Assignee: Arizona Board of Regents on Behalf of the University of Arizona, a body corporate, Tucson, AZ (US)

( * ) Notice: Subject to any disclaimer, the term of this patent is extended or adjusted under 35 U.S.C. 154(b) by 0 days.

(21) Appl. No.: 15/044,924

(22) Filed: Feb. 16, 2016

(65) Prior Publication Data
US 2016/0166639 A1 Jun. 16, 2016

Related U.S. Application Data

(63) Continuation-in-part of application No. PCT/US2014/051143, filed on Aug. 14, 2014.

(60) Provisional application No. 61/865,958, filed on Aug. 14, 2013.

(51) Int. Cl.
A61K 38/00 (2006.01)
A61K 49/00 (2006.01)
C07K 14/00 (2006.01)
A61K 38/18 (2006.01)
C07K 14/475 (2006.01)
C07K 14/48 (2006.01)
C07K 14/575 (2006.01)
A61K 38/17 (2006.01)
A61K 38/22 (2006.01)
C12N 5/0793 (2010.01)
G01N 33/68 (2006.01)

(52) U.S. Cl.
CPC ...... A61K 38/1709 (2013.01); A61K 38/2278 (2013.01); C07K 2317/21 (2013.01); C07K 2317/41 (2013.01); C12N 5/0619 (2013.01); G01N 33/6896 (2013.01); G01N 2800/2814 (2013.01); G01N 2800/2821 (2013.01)

(58) Field of Classification Search
CPC .... A61K 2300/00; A61K 38/27; A61K 35/12; A61K 38/00; A61K 35/30; C07K 14/475; A61L 2300/414; C12N 2501/35; C12N 5/019; G01N 33/5058; G01N 2333/70571; G01N 33/6896; G01N 33/0406; Y02P 20/52
See application file for complete search history.

(56) References Cited

U.S. PATENT DOCUMENTS

| | | | | |
|---|---|---|---|---|
| 7,521,424 B2 * | 4/2009 | Rosen | ............ | A61K 38/38 514/1.1 |
| 7,569,384 B2 * | 8/2009 | Rosen | ............ | C07K 14/765 435/252.3 |
| 7,803,764 B2 * | 9/2010 | Polt | ............ | A61K 38/08 514/17.5 |
| 8,143,026 B2 * | 3/2012 | Rosen | ............ | C07K 14/765 435/254.11 |
| 8,916,517 B2 * | 12/2014 | Coy | ............ | A61K 33/24 514/1.4 |
| 9,006,181 B2 * | 4/2015 | Arimura | ............ | C07K 14/57563 514/15.4 |
| 2004/0038888 A1 * | 2/2004 | Mercer | ............ | A61K 38/1767 424/141.1 |
| 2004/0092432 A1 * | 5/2004 | During | ............ | C07K 14/605 514/1.1 |
| 2006/0014254 A1 * | 1/2006 | Haseltine | ............ | A61K 38/38 435/69.7 |
| 2007/0027306 A1 * | 2/2007 | Rosen | ............ | C07K 14/765 530/399 |
| 2007/0048282 A1 * | 3/2007 | Rosen | ............ | C07K 14/765 424/85.7 |
| 2007/0111932 A1 * | 5/2007 | Andersen | ............ | A61K 38/1808 435/325 |
| 2008/0085860 A1 * | 4/2008 | Bokvist | ............ | C07K 14/57563 514/7.3 |

(Continued)

FOREIGN PATENT DOCUMENTS

| | | | | |
|---|---|---|---|---|
| EP | 768090 | * | 4/1997 | ............ A61K 38/22 |
| WO | WO2006023358 | * | 3/2006 | ............ C07K 14/435 |

(Continued)

OTHER PUBLICATIONS

Egleton et al., Teterhedron: Asymmetry, 2005; 16:65-75.*

(Continued)

Primary Examiner — Chang-Yu Wang
(74) Attorney, Agent, or Firm — Don D. Cha; Hamilton DeSanctis & Cha, LLP

(57) ABSTRACT

A glycosylated pleiotropic peptide pituitary adenylate cyclase-activating polypeptide (PACAP) which can both agonize $PAC_1$ receptors, causing neuroprotective effects, and antagonize VPAC receptors, causing anti-inflammation in several models of acute neuronal damage and neurodegenerative diseases, including ALS, PD, migraines, and certain forms of dementia, is described. Also described is a method of relieving symptoms of ALS, PD, migraines, and certain forms of dementia, comprising administering to a subject in need thereof an effective amount of a glycosylated PACAP.

14 Claims, 4 Drawing Sheets
Specification includes a Sequence Listing.

(56) References Cited

U.S. PATENT DOCUMENTS

| | | | | |
|---|---|---|---|---|
| 2010/0048472 | A1* | 2/2010 | Rosen | A61K 38/38 514/6.9 |
| 2010/0093627 | A1* | 4/2010 | Rosen | C07K 14/765 514/6.9 |
| 2010/0184678 | A1* | 7/2010 | Bevec | A61K 38/08 514/1.1 |
| 2010/0197588 | A1* | 8/2010 | Bevec | A61K 38/2235 514/5.5 |
| 2012/0309683 | A1* | 12/2012 | Coy | A61K 38/13 514/15.4 |
| 2013/0065816 | A1 | 3/2013 | Coy et al. | 514/1.4 |
| 2013/0096050 | A1* | 4/2013 | Shandler | C07K 14/57563 514/1.7 |
| 2016/0122406 | A1* | 5/2016 | Coy | C07K 14/57563 424/1.61 |

FOREIGN PATENT DOCUMENTS

| | | | | |
|---|---|---|---|---|
| WO | WO2006023367 | * | 3/2006 | C07K 14/435 |
| WO | WO2011054001 | * | 5/2011 | A61K 38/16 |
| WO | WO2014197909 | * | 12/2014 | A61K 38/00 |

OTHER PUBLICATIONS

Vaudry et al. Pharmcol. Rev. 2009; 61: 283-357.*
Sola et al. BioDrugs, 2010; 24: 9-21.*
Vaudry et al. Pharmacol. Rev. 2009; 61: 283-357.*
U.S. Appl. No. 15/752,157, filed Feb. 2018.*
International Search Report and Written Opinion issued in application no. PCT/US2014/051143, dated Dec. 5, 2014 (6 pgs).
International Preliminary Report on Patentability issued in application no. PCT/US2014/051143, dated Feb. 25, 2016 (5 pgs).
McNally et al., G. P.; Akil, H. Opioid peptides and their receptors: overview and function in pain modulation. In Neuropsychopharmacology: the Fifth Generation of Progress, Davis, K. L.; Charney, D.; Coyle, J. T.; Nemeroff, C. Eds, Lippincott Williams & Wilkins, Philadelphia, 2002, Chapter 3, pp. 35-46 (12 pgs).
Adessi, C.; Soto, C., Converting a Peptide into a Drug: Strategies to Improve Stability and Bioavailability, Cur. Med. Chem. 2002, 9, 963-978 (16 pgs).
Reese, T. S.; Karnovsky, M. J., Fine Structural Localization of Blood-Brain Barrier to Exogenous Peroxidase, J. Cell. Biol. 1967, 34, 207-217 (11 pgs).
Pardridge, W. M. Introduction to the Blood-Brain Barrier, Brain Drug Targeting, Chapter 3, Lipid mediated transport and carrier-mediated transport of small molecules, Cambridge University Press: New York, 1993 (26 pgs).
Pardridge, W. M. Introduction to the Blood-Brain Barrier, Chapter 7, Protein Neurotherapeutics and peptide radiopharmaceuticals, Cambridge University Press: New York, 1993 (18 pgs).
Greig, N. H.; Fredericks, W. R.; Holoway, H. W.; Soncrant, T. T.; Rapoport, S. I., Delivery of Human Interferon-Alpha to Brain by Transient Osmotic Blood-Brain Modification in the Rat, J. Pharmacol. Exp. Ther. 1988, 245, 581-586 (6 pgs).
Hruby, V. J.; Mosberg, H. I., Conformational and Dynamic Considerations in Peptide Structure-Function Studies, Peptides 1982, 3, 329-336 (8 pgs).
Mosberg, H. I., Hurst, R., Hruby, V. J.; Galligan, J. J.; Burks, T. F.; Gee, K.; Yamamura, H. I., [D-PEN2, L-Cysienkephalinamide and [D-PEN2, D-CYS1ENKEPHALINAMIDE, Conformationally Constrained Cyclic Enkephalinamide Analogs With Delta Receptor Specificity, Biochem. Biophys. Res. Commun. 1982, 106, 506-512 (7 pgs).
Hruby, V. J., Conformational and Topographical Considerations in the Design of Biologically Active Peptides, Biopolymers 1993, 33, 1073-1082 (10 pgs).
Bodor, N.; Prokai, L.; Wu, W. M.; Farag, H.; Jonalagadda, S.; Kawamura, M.; Simpkins, J., a Strategy for Delivering Peptides into the Central Nervous System by Sequential Metabolism, Science 1992, 257, 1698-1700 (4 pgs).

Rousselle, C.; Clair, P.; Lefauconnier, J. M.; Kaczorek, M.; Scherrmann, J. M.; Temsamani, J., New Advances in the Transport of Doxorubicin through the Blood-Brain Barrier by a Peptide Vector-Mediated Strategy, Mol. Pharmacol. 2000, 57, 679-686 (8 pgs).
Albert, R.; Marbach, P.; Bauer, W.; Briner, U.; Fricker, G.; Bruns, C.; Pless, J., Sdz Co 611: a Highly Potent Glycated Analog of Somatostatin with Improved Oral Activity, Life Sci. 1993, 53, 517-525 (9 pgs).
Polt, R.; Porreca, F.; Szabo, L. Z.; Bilsky, E. J.; Davis, P.; Abbruscato, T. J.; Davis, T. P.; Harvath, R.; Yamamura, H. I.; Hruby, V. J., Glycopeptide enkephalin analogues produce analgesia in mice: Evidence for penetration of the blood-brain barrier, Proc. Natl. Acad. Sci. Usa 1994, 91, 7114-7118 (5 pgs).
Negri, L.; Lattanzi, R.; Tabacco, F.; Orru, L.; Severini, C.; Scolaro, B.; Rocchi, R., Dermorphin and Deltorphin Glycosylated Analogues: Synthesis and Antinociceptive Activity after Systemic Administration, J. Med. Chem. 1999, 42, 400-404 (5 pgs).
Tomatis, R.; Marastoni, M.; Balboni, G.; Guerrini, R.; Capasso, a.; Sorrentino, L.; Santagada, V.; Caliendo, G.; Lazarus, L. H.; Salvadori, S., Synthesis and Pharmacological Activity of Deltorphin and Dermorphin-Related Glycopeptides, J. Med. Chem. 1997, 40, 2948-52 (5 pgs).
Egleton, R. D.; Mitchell, S. A.; Huber, J. D.; Palian, M. M.; Polt, R.; Davis, T. P., Improved Blood-Brain Barrier Penetration and Enhanced Analgesia of an Opioid Peptide by Glycosylation, J. Pharmacol. Exp. Ther. 2001, 299, 967-972 (6 pgs).
Bilsky, E. J.; Egleton, R. D.; Mitchell, S. A.; Palian, M. M.; Davis, P. Huber, J. D.; Jones, H.; Yamamura, H. I.; Janders, J.; Davis, T. P.; Porreca, F.; Hruby, V. J.; Polt. R., Enkephalin Glycopeptide Analogues Produce Analgesia with Reduced Dependence Liability, J. Med. Chem. 2000, 43, 2586-2590 (5 pgs).
Elmagbari, N. 0.; Egleton, R. D.; Palian, M. M.; Lowery, J. J.; Schmid, W. R.; Davis, P.; Navratilova, E.; Dhanasekaran, M.; Keyari, C. M.; Yamamura, H. I.; Porreca, F.; Hruby, V. J.; Polt, R.; Bilsky, E. J., Antinociceptive Structure-Activity Studies with Enkephalin-Based Opioid Glycopeptides, J. Pharmacol. Expt. Ther. 2004, 311, 290-297 (8 pgs).
Palian, M. M.; Boguslaysky, V. I.; O'Brien, D. F.; Polt, R., Glycopeptide-Membrane Interactions: Glycosyl Enkephalin Analogues Adopt Turn Conformations by Nmr and Cd in Amphipathic Media, J. Am. Chem. Soc. 2003, 125, 5823-5831 (9 pgs).
Susaki, H.; Suzuki, K.; Yamada, H.; Okuno, S.; Watanabe, H. K., Renal targeting of arginine-vasopressin by modification with carbohydrates at the tyrosine side chain, Biol, Pharm. Bull. 1999, 22, 1094-1098 (6 pgs).
Suzuki, K.; Susaki, H.; Okuno, S.; Sugiyama, Y., Renal Drug Targeting Using a Vector Alkylglycoside, J. Pharmacol. Exp. Ther. 1999, 288, 57-64 (8 pgs).
Suzuki, K., Susaki, H.; Okuno, S.; Yamada, H.; Watanabe, H. K.; Sugiyama, Y., Specific Renal Delivery of Sugar-Modified Low-Molecular-Weight Peptides, J. Pharmacol. Exp, Ther. 1999, 288, 888-897 (10 pgs).
Egleton, R. D.; Mitchell, S. A.; Huber, J. D.; Janders, J.; Stropova, D.; Polt, R.; Yamamura, H. I.; Hruby, V. J.; Davis, T. P., Improved bioavailability to the brain of glycosylated Met-enkephalin analogs, Brain Res. 2000, 881, 37-46 (10 pgs).
Gysin, B.; Schwyzer, R., Head Group and Structure Specific Interactions of Enkephalins and Dynorphin with Liposomes: Investigation by Hydrophobic Photolabeling, Arch. Biochem. Biophys. 1983, 225, 467-474 (8 pgs).
Lee, N. M.; Smith, a. P., Minireview a Protein-Lipid Model of the Opiate Receptor, Life Sci. 1980, 26, 14591464 (6 pgs).
Graf, L.; Cseh, C.; Barat, E.; Ronai, a. Z; Szekely, J.; Kennesey, a.; Bajusz, S., Structure-Function Relationships in Lipotropins, Ann. n. Y. Acad. Sci. 1977, 297, 63 (21 pgs).
Schwyzer, R., Molecular Mechanism of Opioid Receptor Selection, Biochemistry 1986, 25, 6336-6342 (8 pgs).
Taylor, J. W.; Osterman, D. G.; Miller, R. J.; Kaiser, E. T., Design and Synthesis of a Model Peptide with f3-Endorphin-Like Properties, J. Am. Chem. Soc., 1981, 103, 6965-6966 (2 pgs).
Taylor, J. W.; Kaiser, E. T., Opioid receptor selectivity of peptide models of (3-endorphin, Int. J. Pept. Protein Res. 1989, 34, 75-80 (6 pgs).

(56) References Cited

OTHER PUBLICATIONS

Blanc, J. P.; Taylor, J. W.; Miller, R. J.; Kaiser, E. T., Examination of the Requirement for an Amphiphilic Helical Structure in (3-Endorphin through the Design, Synthesis, and Study of Model Peptides, J. Biol. Chem. 1983, 258, 8277-8284 (9 pgs).

Taylor, J. W.; Miller, R. J.; Kaiser, E. T., Characterization of an Amphiphilic Helical Structure in 13-Endorphin through the Design, Synthesis, and Study of Model Peptides, J. Biol. Chem. 1983, 258, 4464-4471 (9 pgs).

Taylor, J. W.; Miller, R. J.; Kaiser, E. T., Structural Characterization of13-Endorphin through the Design, Synthesis, and Study of Model Peptides, Mol. Pharmacol. 1982, 22, 657-666 (10 pgs).

Taylor, J. W.; Kaiser, E. T., Structure-Function Analysis of Proteins through the Design, Synthesis, and Study of Peptide Models, Methods Enzymol. 1987, 154, 473-499 (26 pgs).

Goldstein, a.; Fischli, W.; Lowney, L. I.; Hunkapiller, M.; Hood, L., Porcine Pituitary dynorphin: Complete amino acid sequence of the biologically active heptadecapeptide, Proc. Natl. Acad. Sci. Usa. 1981, 78, 72197223 (5 pgs).

Chavkin, C.; Goldstein, a., Specific receptor for the opioid peptide dynorphin: Structure-activity relationships, Proc. Natl. Acad. Sci. Usa. 1981, 78, 6543-6547 (5 pgs).

Renugopalakrishnan, V.; Rapaka, R. S.; Huang, S.-G.; Moore, S.; Huston, T. B., Dynorphin a (1-13) Peptide Nh Groups are Solvent Exposed: Ft-Ir and 500 MHz 1H Nmr Spectroscopic Evidence, Biochem. Biophys, Res. Commun. 1988, 151, 1220-1225 (6 pgs).

Zhou, N.; Gibbons, W. A., a 1H Nuclear Magnetic Resonance Study of the Opioid Peptide Dynorphin-(1-13) in Aqueous Solution, J. Chem. Soc., Perkin Trans. 1986, 2, 637-644 (8 pgs).

Maroun, R.; Mattice, W. L., Solution Conformations of the Pituitary Opioid Peptide Dynorphin-(1-13), Biochem. Biophys. Res. Commun. 1981, 103, 442-446 (5 pgs).

Spadaccini, R.; Crescenzi, 0.; Picone, D.; Tancredi, T.; Temussi, a., Solution Structure of Dynorphin a (1-17): a Nmr Study in a Cryoprotective Solvent Mixture at 278 K, J. Peptide Sci. 1999, 5, 306-312 (7 pgs).

Tessmer, M.; Kallick, D., Nmr and Structural Model of Dynorphin a (1-17) Bound to Dodecylphosphocholine Micelles, a. Biochemistry 1997, 36, 1971-1981 (11 pgs).

Lung, F-D. T.; Collins, N.; Stropova, D.; Davis, P.; Yamamura, H. I.; Porreca, F.; Hruby, V. J., Design, Synthesis, and Biological Activities of Cyclic Lactam Peptide Analogues of Dynorphin a(1-11)-NH21, J. Med. Chem. 1996, 39, 1136-1141 (6 pgs).

Polt, R.; Szabo, L.Z.; Treiberg, J.; Li, Y.; Hruby, V.J. (1992) General Methods for a or p. 0-Ser/Thr Glycosides and Glycopeptides. Solid-Phase Synthesis of 0-Glycosyl Cyclic Enkephalin Analogues. J Am. Chem. Soc. 114, 10249-10258.

Mitchell, S.A.; Pratt, M.R.; Hruby, V.J.; Polt, R. (2001) Solid-Phase Synthesis of 0-Linked Glycopeptide Analogues of Enkephalin. J Org. Chem. 66, 2327-2342 (16 pgs).

Lefever, M.R.; Szabo, L.Z.; Anglin, B.; Ferracane, M.; Hogan, J.; Cooney, L.; Polt, R. (2012) Glycosylation of a-amino acids by sugar acetate donors with InBr3. Minimally competent Lewis acids. Carbohydr. Research 351, 121-125 (5 pgs).

Robberecht, P.; Gourlet, P.; De Neef, P.; et al. (1992) Structural requirements for the occupancy of pituitary adenylate-cyclase-activating-peptide (Pacap) receptors and adenylate cyclase activation in human neuroblastoma Nb-Ok-1 cell membranes. Discovery of Pacap(6-38) as a potent antagonist. Eur. J Biochem. 207, 239-246 (8 pgs).

Gourlet et al., Fragments of pituitary adenylate cyclase activating polypeptide discriminate between type I and Ii recombinant receptors, European Journal of Phamacology 287 (1995) 7-11, (5 pgs).

Zhang, C.; Miller, W.; Valenzano, K. J.; Kyle, D. J., Novel, Potent Orl-1 Receptor Agonist Peptides Containing a-Helix-Promoting Conformational Constraints, J. Med. Chem. 2002, 45, 5280-5286 (7 pgs).

Banks, W.A., Delivery of Peptides to the Brain: Emphasis on Therapeutic Development. Peptide Science 90, 589-594 (2008) (6 pgs).

Banks, W.A.; Kastin, a.J.; Komaki, G.; Arimura, a. Passage of pituitary adenylate cyclase activating polypeptide1..27 and pituitary adenylate cyclase activating polypeptide1_38 across the blood-brain barrier. J. Pharm. Exp. Therap. 267, 690-696 (1993) (7 pgs).

Dogrukol-Ak, D.; Tore, F.; Tuncel, N., Passage of Vip/Pacap/secretin family across the blood-brain barrier: therapeutic effects. Curr. Pharm. Des. 10, 1325-1340 (2004) (18 pgs).

Yue X., Falk T,, Zuniga L.A., Szabo L., Porreca F., Polt R., Sherman S.J., Effects of the novel glycopeptide opioid agonist Mmp-2200 in preclinical models of Parkinson's disease. Brain Research, 1413: 72-83 (2011) (12 pgs).

Mabrouk, 0.S.; Falk, T.; Sherman, S.J.; Kennedy, R.T.; Polt, R. Cns penetration of the opioid glycopeptide Mmp-2200: a microdialysis study. Neurosci. Lett. 531, 99-103 (2012) (5 pgs).

972 (2001) (6 pgs).

Li, Y.; Lefever, M.R.; Muthu, D.; Bidlack, J.M.; Bilsky, E.J.; Polt, R. Opioid glycopeptide analgesics derived.

226 (2012) (22 pgs).

Dejda, a.; Sokotowska, P.; Nowak, J.Z. Neuroprotective potential of three neuropeptides Pacap, Vip and Phi.

320 (2005) (15 pgs).

Waschek J.A. Vip and Pacap: neuropeptide modulators of Cns inflammation, injury, and repair. British.

523 (2013) (12 pgs).

Watson M.B., Nobuta H., Abad C., Lee S.K., Bala N., Zhu C., Richter F., Chesselet M.F., Waschek J.A. Pacap deficiency sensitizes nigrostriatal dopaminergic neurons to paraquat-induced damage and modulates central and.

286 (2013) (10 pgs).

Ringer, C.; Baiting, L.S.; Schafer, M.K.H.; Eiden, L.E.; Weihe, E.; Schatz, B. Pacap signaling exerts opposing effects on neuroprotection and neuroinflammation during disease progression in the Sod.] (G93A) mouse model of amyotrophic lateral sclerosis. Neurobiol. Disease 54, 32-42 (2013) (11 pgs).

Dufes, C., Peptide and Protein Delivery, Chapter 6: Brain Delivery of Peptides and Proteins, Academic Press: London (2011) (12 pgs).

* cited by examiner

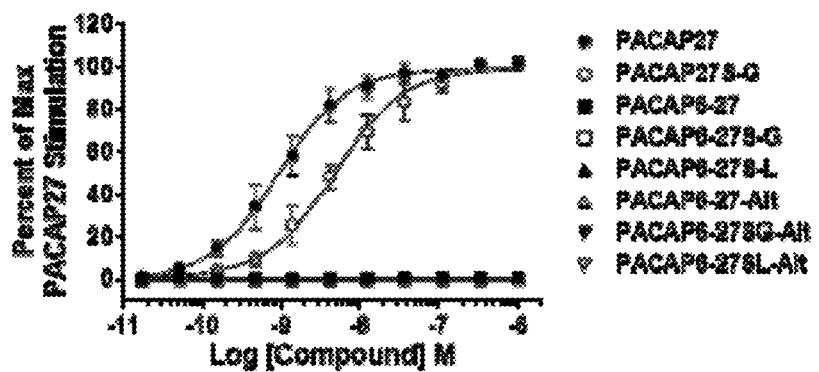
FIGURE 6
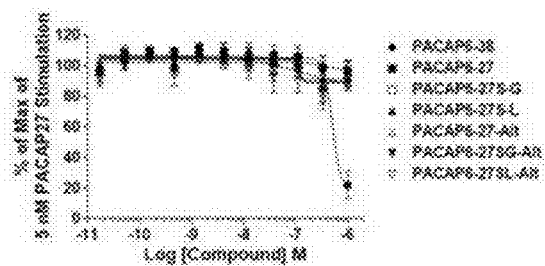
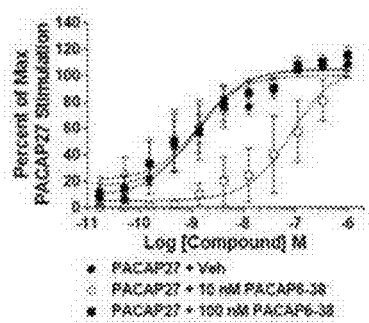
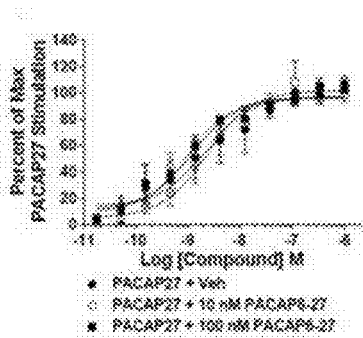

GLYCOSYLATED PACAP/VIP ANALOGUES WITH ENHANCED CNS PENETRATION FOR TREATMENT OF NEURODEGENERATIVE DISEASES

CROSS REFERENCE TO RELATED APPLICATION

This application is a Continuation-in-part (CIP) of the US National Phase of PCT Application PCT/US2014/051143 filed Aug. 14, 2014, which claims priority from U.S. Provisional Application Ser. No. 61/865,958, filed Aug. 14, 2013, the contents of which are incorporated herein by reference.

STATEMENT REGARDING FEDERALLY FUNDED RESEARCH

This invention was made with Government support under Grant No. CHE-9526909 awarded by the National Science Foundation, Grant No. R01NS52727 and Grant No. R01NS091238, both awarded by the Department of Health and Human Services, National Institutes of Health, National Institute of Neurological Disorders and Stroke. The Government has certain rights in the invention.

BACKGROUND OF THE INVENTION

The present invention relates to glycopeptides for treatment of neurodegenerative diseases. The invention is particularly applicable in connection for the treatment of amyotrophic lateral sclerosis (ALS) and Parkinson's Disease (PD), Alzheimer's Disease (AD), Huntington's Disease (HD), migraine attacks, traumatic brain injury and stroke, as well as certain forms of dementia and will be described in connection with such utility, although other utilities are contemplated.

Endogenous opioid peptides, lumped together under the generic term endorphins, have been the subject of intense study since their discovery in the mid 1970's[1]. Neuropeptides have the potential for extremely selective pharmacological intervention with fewer side effects. If these naturally occurring opioid peptides and their derivatives could be rendered permeable to the blood-brain barrier (BBB), then a new vista of psychopharmacology would be opened to exploration and exploitation. After three decades of research, many potent and selective opioid agonists have been developed, and stability problems have been largely overcome. The remaining problem that prevents the use of opioid peptides as drugs is poor bioavailability, which is primarily due to poor penetration of the BBB[2]. The BBB is composed of endothelial cells in the cerebrovascular capillary beds[3]. The BBB acts as a lipophilic barrier to undesired chemical substances, and admits vital nutrients for proper function of the CNS[4]. The flow is bi-directional, allowing for export of materials from the CNS (efflux transport) and the import of materials from the blood (influx transport). The BBB represents not only a physical obstacle, but a metabolic one as well, possessing both oxidative enzymes and peptidases such as aminopeptidase, arylamidase and enkephalinase. Thus, metabolically unstable substances (e.g. peptides) are generally degraded before they reach the CNS. It should also be noted that entry to the CNS does not guarantee that a drug will accumulate in useful concentrations, as many peptides are rapidly exported back to the bloodstream[5]. Several strategies have been reported to overcome the BBB penetration problem, including substitution of unnatural amino acids[6], the use of conformational constraints,[7] and the addition of lipophilic side chains or other transport vectors[8]. Glycosylation has proven to be a successful methodology to improve both the stability and bioavailability of short peptide "messages" by incorporation of the peptide pharmacophore into a glycopeptide[9]. Previous BBB penetration studies with opioid glycopeptide agonists based on enkephalins have shown up to 3-fold increases in the rate of brain delivery of these compounds compared with the unglycosylated parent peptides[10]. Recent studies with glycopeptides in artificial membrane systems indicate that amphipathicity of the glycopeptides is an important factor in BBB penetration[11]. In addition, there is evidence that suggests that the type of glycosylation can alter tissue distribution patterns[12], BBB penetration[13] and peptide/receptor interactions[11, 14].

Endogenous Opioid Peptides. The endogenous neuropeptide ß-endorphin is a 31 residue naturally occurring opioid peptide agonist that binds to μ and δ receptors. Its N-terminal 5 residues are identical to the Met-Enkephalin sequence, and may be considered to be the pharmacophore or "opioid message." It was shown some time ago that the C-terminal region of ß-endorphin has an amphipathic α-helical structure that plays a role in the receptor binding and opioid agonism[15] and may induce resistance to proteolysis[16]. According to Schwyzer, the N-terminal sequence is the essential "message," and the C-terminal helical region is the "address" that limits delivery of the message to a subset of otherwise available opioid receptors[17]. Kaiser and co-workers proposed that ß-endorphin consists of the Met-enkephalin peptide sequence at the N-terminus, a hydrophilic linker region from residues 6 through 12, and an amphiphilic helical region between the helix breaker residues Pro(13) and Gly(30)[18]. This was later proven by synthesizing a number of ß-endorphin mimics with artificial C-terminal helical regions with amphipathic character[19]. These de novo amphipathic helices were not homologous with the ß-endorphin C-terminal region, and they were shown to be largely α-helical by circular dichroism (CD) measurements. These hybrid structures showed good opioid agonism in vitro when compared to ß-endorphin. These studies strongly suggested that the overall amphipathicity of the C-terminal helix plays a key role in the selectivity of these compounds, rather than the identity of specific amino acid residues present in the C-terminal[20]. Dynorphin A (1-17) is also an endogenous opioid peptide, but it binds preferentially to the κ opioid receptor and has an N-terminal message segment identical to Leu-Enkephalin[21]. It has been suggested that an address sequence in the C-terminal region imparts selectivity for κ receptors[22]. Dynorphin A displayed an extended and/or random coil structure when subjected to structural analysis by various spectroscopic measurements[23]. A 2D (1) H-NMR study in DPC micelle shows that Dynorphin A(1-17) contains a less ordered N-terminal segment, a well defined α-helix segment spanning between Phe(4) and Pro(10) or Lys(11), and a ß-turn from Trp(14) to Gln(17)[24]. Based on NMR results, the authors concluded that both the α-helix and the C-terminal ß-turn are due to dynorphin-micelle interactions, and may be important structural features of the full-length peptide when bound to the cell membrane in vivo. Studies by Luna[25] also support the notion that a helical structure in the message segment of Dynorphin A(1-17) is significant. The biological importance of helical C-terminal address segments in larger opioid peptides has been further supported by the recent work by Kyle and co-workers[32]. They successfully synthesized several potent nociceptin (NC) peptide analogs exploiting the α-helix-promoting residues α-aminoisobutyric acid (Aib) and N-methyl alanine (MeAla) at the C-terminus of NC. Nociceptin is the endogenous ligand for the recently identified opioid receptor-like 1 receptor (ORL-1). Thus, it seems logical to approach the design of opioid agonist ß-endorphin or dynorphin peptide analogs by combining C-terminal amphipathic helical address segments that can also promote BBB, for penetration by virtue of glycosylation. The foregoing discussion of the prior art derives from our prior U.S. Pat. No. 7,803,764 with Bilsky, in which we provide certain amphipathic glycopeptides which are capable of crossing the blood-brain-barrier (BBB), for treating a variety of neurological and behavior disorders including pain, anxiety, depression, obesity, anorexia nervosa, phobias, schizophrenia, Parkinson's Disease (PD) and Alzheimer's Disease (AD).

It is an object of the present invention to provide glycopeptides that penetrate the blood-brain-barriers (BBB) for treatment of neurodegenerative diseases such as amyotrophic lateral sclerosis (ALS), Parkinson's Disease (PD), Alzheimer's Disease (AD), Huntington's Disease (HD), migraine attacks, traumatic brain injury and stroke, as well as certain forms of dementia.

SUMMARY OF THE INVENTION

More particularly, we have discovered a new variation of glycosylated pleiotropic peptides, pituitary adenylate cyclase-activating polypeptide (PACAP) or vasoactive intestinal peptide (VIP), which can both agonize $PAC_1$ $VIP_1$ & $VIP_2$ receptors, causing neuroprotective effects, or in their N-terminal truncated forms, can antagonize these receptors, having anti-inflammatory effects in several models of acute neuronal damage and neurodegenerative diseases, including ALS, PD, AD, HD, migraines, traumatic brain injury, stroke and certain forms of dementia.

The present invention also provides a method of relieving symptoms of ALS, PD, AD, HD, migraines, traumatic brain injury, stroke and certain forms of dementia, comprising administering to a subject in need thereof an effective amount of a glycosylated PACAP or VIP analogue.

Further features and advantages of the present invention can be seen from the following detailed description, taken in connection with the accompanying drawings wherein.

Figure 3:
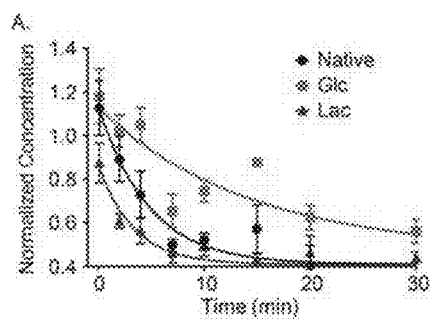
Figure 4:
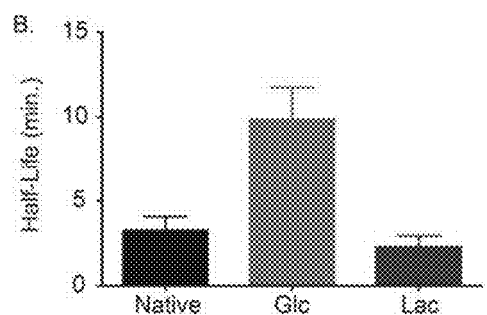
Figure 5:
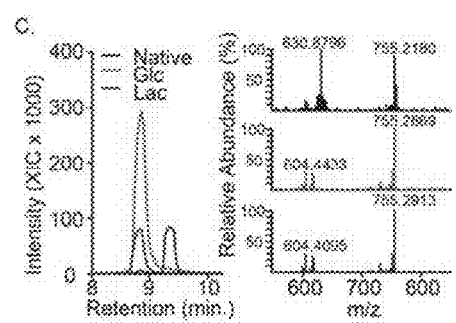

FIG. 3 plots stability of $PACAP_{1-27}$, $PACAP_{1-27-S-G}$ and $PACAP_{1-27-S-L}$;

FIG. 4 shows Serine glucoside increase in mouse serum compared to native peptide $PACAP_{1-27}$ and the corresponding lactoside;

FIG. 5 shows $MS^2$ fragmentation patterns for native PACAP and the fragmentation patterns of Glc and Lac;

FIG. 6 shows $PAC_1$-CHO calcium flux of $PACAP_{1-27}$ and various truncated derivatives;

FIGS. 7a-7c show representation curves of PACAP in various conditions; and

FIGS. 8a-8d show PC12 cell morphology after vehicle versus PACAP treatment at various solutions.

DETAILED DESCRIPTION OF THE INVENTION

Before the compositions and methods of the disclosure are described, it is to be understood that this disclosure is not limited to the particular processes, compositions, or methodologies described, as these may vary. It is also to be understood that the terminology used in the description is for the purpose of describing the particular versions or embodiments only, and is not intended to limit the scope of the present disclosure which will be limited only by the appended claims.

It must be noted that, as used herein, and in the appended claims, the singular forms "a", "an" and "the" include plural reference unless the context clearly dictates otherwise. Unless defined otherwise, all technical and scientific terms used herein have the same meanings as commonly understood by one of ordinary skill in the art. Although any methods similar or equivalent to those described herein can be used in the practice or testing of embodiments of the present disclosure, the preferred methods are now described. All publications and references mentioned herein are incorporated by reference. Nothing herein is to be construed as an admission that the disclosure is not entitled to antedate such disclosure by virtue of prior disclosure.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. "Administering" a composition may be accomplished by oral or rectal administration, injection, infusion, inhalation, absorption or by any method in combination with other known techniques. Such combination techniques include heating, radiation and ultrasound.

The term "improves" is used to convey that the present disclosure changes the appearance, form, characteristics and/or physical attributes of the tissue to which it is being provided, applied or administered. "Improves" may also refer to the overall physical state of an individual to whom an active agent has been administered. For example, the overall physical state of an individual may "improve" if one or more symptoms of a neurodegenerative disorder are alleviated by administration of an active agent, and is not limited to increased stability or BBB penetration.

As used herein, the term "therapeutic" means an agent utilized to treat, combat, ameliorate or prevent an unwanted condition or disease of a patient.

The terms "therapeutically effective amount" or "therapeutic dose" as used herein are interchangeable and may refer to the amount of an active agent or pharmaceutical compound or composition that elicits a biological or medicinal response in a tissue, system, animal, individual or human that is being sought by a researcher, veterinarian, medical doctor or other clinician. A biological or medicinal response may include, for example, one or more of the following: (1) preventing a disease, condition or disorder in an individual that may be predisposed to the disease, condition or disorder but does not yet experience or display pathology or symptoms of the disease, condition or disorder, (2) inhibiting a disease, condition or disorder in an individual that is experiencing or displaying the pathology or symptoms of the disease, condition or disorder or arresting further development of the pathology and/or symptoms of the disease, condition or disorder, and (3) ameliorating a disease, condition or disorder in an individual that is experiencing or exhibiting the pathology or symptoms of the disease, condition or disorder or reversing the pathology and/or symptoms experienced or exhibited by the individual.

The term "treating" may be taken to mean prophylaxis of a specific disorder, disease or condition, alleviation of the symptoms associated with a specific disorder, disease or condition and/or prevention of the symptoms associated with a specific disorder, disease or condition. In some embodiments, the term refers to slowing the progression of the disorder, disease or condition or alleviating the symptoms associated with the specific disorder, disease or condition. In some embodiments, the term refers to slowing the progression of the disorder, disease or condition. In some embodiments, the term refers to alleviating the symptoms associated with the specific disorder, disease or condition. In some embodiments, the term refers to restoring function, which was impaired or lost due to a specific disorder, disease or condition.

The term "patient" generally refers to any living organism to which the compounds described herein, are administered and may include, but is not limited to, any non-human mammal, primate or human. Such "patients" may or may not be exhibiting the signs, symptoms or pathology of the particular diseased state.

The term "pharmaceutical composition" shall mean a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan. A pharmaceutical composition may, for example, contain an AKT inhibitor or a pharmaceutically acceptable salt of an AKT inhibitor as the active ingredient.

For the purposes of this disclosure, a "salt" is any acid addition salt, preferably a pharmaceutically acceptable acid addition salt, including but not limited to, halogenic acid salts such as hydrobromic, hydrochloric, hydrofluoric and hydroiodic acid salt; an inorganic acid salt such as, for example, nitric, perchloric, sulfuric and phosphoric acid salt; an organic acid salt such as, for example, sulfonic acid salts (methanesulfonic, trifluoromethan sulfonic, ethanesulfonic, benzenesulfonic or p-toluenesulfonic), acetic, malic, fumaric, succinic, citric, benzoic, gluconic, lactic, mandelic, mucic, palmoic, pantothenic, oxalic and maleic acid salts; and an amino acid salt such as aspartic or glutamic acid salt. The acid addition salt may be a mono- or di-acid addition salt, such as a di-hydrohalogenic, di-sulfuric, di-phosphoric or di-organic acid salt. In all cases, the acid addition salt is used as an achiral reagent which is not selected on the basis of any expected or known preference for interaction with or precipitation of a specific optical isomer of the products of this disclosure.

"Pharmaceutically acceptable salt" is meant to indicate those salts which are, within the scope of sound medical judgment, suitable for use in contact with the tissues of a patient without undue toxicity, irritation, allergic response and the like, and are commensurate with a reasonable benefit/risk ratio. Pharmaceutically acceptable salts are well known in the art. For example, Berge et al. (1977) J. Pharm. Sciences, Vol 6. 1-19, which is hereby incorporated by reference in its entirety, describes pharmaceutically acceptable salts in detail.

As used herein, the term "daily dose amount" refers to the amount of pramipexole per day that is administered or prescribed to a patient. This amount can be administered in multiple unit doses or in a single unit dose, in a single time during the day or at multiple times during the day.

A "dose amount" as used herein, is generally equal to the dosage of the active ingredient, which may be administered per day. For example, an effective dose amount may be between about 0.1 and 10 milligrams per kilo, administered 1-2 times a day.

The term "unit dose" as used herein may be taken to indicate a discrete amount of the therapeutic composition that contains a predetermined amount of the active compound. The amount of the active compound is generally equal to the dosage of the active ingredient, which may be administered one or more times per day. For example, the unit dose may be a fraction of the desired daily dose which may be given in fractional increments, such as, for example, one-half or one-third the dosage.

The present invention is based on the recent discovery that Penetration of the blood-brain barrier (BBB) by peptides[32, 33, 34, 35, 36, 37] as well as their stability in vivo 38 is significantly enhanced by glycosylation.[39] As used herein, the terms "glycosylation" and "glycosylated" means that an amino acid residue is functionalized with a glycosyl group. A glycosyl group is composed of saccharide units. These terms are well-known in the field of peptide and protein chemistry and have such meanings as used herein. In preferred embodiments, the glycosyl group has at most 8 saccharide units. More preferably, the glycosyl group has at most 4 saccharide units. In another embodiment, the glycosyl group is at most a disaccharide, i.e., the glycosyl group has at most 2 saccharide units. Thus, the total number of saccharide units may be from 1 to 8, inclusive of all specific values and ranges therebetween. Examples of glycosyl groups include ß-D-glucose, ß-maltose, ß-lactose, ß-melibiose and ß-maltotriose. Other examples include sucrose, trehalose, saccharose, maltose, cellobiose, gentibiose, isomaltose and primeveose. Other glycosyl groups include galactose, xylose, mannose, manosaminic acid, fucose, GalNAc, GlcNAc, idose, iduronic acid, glucuronic acid and sialic acid.

We have discovered that a new variation of a glycosylated pleiotropic peptide pituitary adenylate cyclase-activating polypeptide (PACAP) has demonstrated neuroprotective and anti-inflammatory properties[40, 41] in several models of acute neuronal damage and neurodegenerative diseases,[42] including the SOD1 (G93A) mouse model of ALS, when injected into the brain.[43] Vasoactive intestinal peptide (VIP) is a closely related secretin-class peptide.

PACAP is a neuropeptide consisting of 38 amino acids with the following amino acid sequence (from the N- to the C-terminus):

(SEQ ID NO: 1)
His-Ser-Asp-Gly-Ile-Phe-Thr-Asp-Ser-Tyr-Ser-Arg-

Tyr-Arg-Lys-Gln-Met-Ala-Val-Lys-Lys-Tyr-Leu-Ala-

Ala-Val-Leu-Gly-Lys-Arg-Tyr-Lys-Gln-Arg-Val-Lys-

Asn-Lys

Two forms of the peptide have been identified: PACAP-38 (SEQ ID NO:2) and PACAP-27 (SEQ ID NO:3) which is shortened at the C-terminus. PACAP-27, which presents a 68% homology to VIP, has the following amino acid sequence (from the N- to the C-terminal amide):

```
                                                (SEQ ID NO: 3)
His-Ser-Asp-Gly-Ile-Phe-Thr-Asp-Ser-Tyr-Ser-Arg-

Tyr-Arg-Lys-Gln-Met-Ala-Val-Lys-Lys-Tyr-Leu-Ala-

Ala-Val-Leu-NH₂
```

PACAP-38 has the following amino acid sequence (from the N- to the C-terminal amide):

```
                                                (SEQ ID NO: 2)
His-Ser-Asp-Gly-Ile-Phe-Thr-Asp-Ser-Tyr-Ser-Arg-

Tyr-Arg-Lys-Gln-Met-Ala-Val-Lys-Lys-Tyr-Leu-Ala-

Ala-Val-Leu₂₇-Gly-Lys-Arg-Tyr-Lys-Gln-Arg-Val-

Lys-Asn-Lys₃₈-NH₂
```

Figure 1:
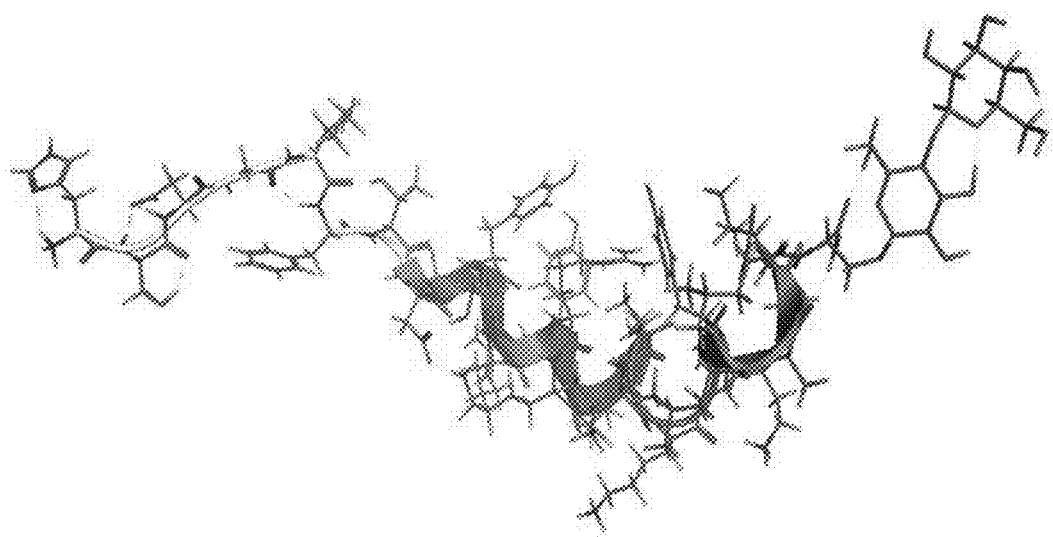
FIG. 1 is a molecular dynamics representation of $PACAP_{1-27}$ that has been modified by replacing the terminal Leucine27 amid with a Serine lactoside amid in accordance with the present invention.

PACAP, which, as noted above exists in 2 forms, either a 27- or 38-amino acid C-terminal peptide amide, was first isolated from ovine hypothalamus, and is known to regulate the development, maintenance, function, and plasticity of the nervous system, providing neuroprotective and neurotrophic support (i.e., see FIG. 1). PACAP has been shown to activate 3 closely-related G protein coupled receptors: $PAC_1$, which has much higher affinity for PACAP, $VPAC_1$ and $VPAC_2$ which bind both PACAP and VIP. They are expressed on neurons, microglia, and also by many other cell types. Constitutive expression of PACAP and its receptor $PAC_1$ may confer neuroprotection to central visceromotor neurons via the $PAC_1$ receptor. PACAP also promotes cytodestructive functions of microglia (M1 amoeboid→M2 hypertrophic phenotype), thought to drive ALS disease progression via the $VPAC_1$ receptor. Thus, the ideal drugs for neuroprotection would be $PAC_1$ agonists at motor neurons to promote neuroprotection in case of ALS, or dopaminergic neurons in case of PD, or hippocampal neurons in case of AD, and in each case $VPAC_1$ antagonists at microglia to reduce inflammation by maintaining the M1 ('alternatively activated'/resolving anti-inflammatory cells) phenotype vs. the M2 (the classical, proinflammatory macrophages) microglia phenotype or Tau-opathies.

In order to develop drugs for treatment of ALS, PD, AD, and HD we synthesized glycopeptide analogs of PACAP with different binding properties to either be only a $PAC_1$ agonist or only a $VPAC_1$ antagonist. Suitable methods for preparing glycopeptides are well-known. The glycopeptides of the present invention were produced using well-known Fmoc-based solid-phase peptide methods, and purified by HPLC. It is preferred that the glycosyl group be linked to the amino acid sequence by an O-linkage to a side chain in the address segment of the sequence. See Tetrahedron Asymmetry 16, 65-75 (2005), incorporated herein by reference, and U.S. Pat. No. 5,727,254.

The overall process was as follows: The C-terminal amino acids were loaded onto Fmoc-Rink resin (Advanced ChemTech, Louisville, Ky., USA) at 0.1 mmol/g resin loading in 25 mL fritted syringes. Initially, the resin was swelled using dimethylformamide (DMF, ~5 mL solvent per gram resin), agitating at RT for two minutes (×2). A solution of 2% DBU and 3% piperidine in DMF (v:v) was introduced and agitated for 5 minutes, refreshed, and agitated for an additional 10 minutes. The resin was washed with DMF (×5), and finally with N-methylpyrrolidine (NMP). In a separate vial, Fmoc-β-OGlc(OAc)₄-Ser-OH (0.12 mmol, 1.2 eq) was dissolved in 5 mL NMP, and HOBt·H₂O (0.13 mmol, 1.3 eq) was added and allowed to mix for 5 minutes. Condensing agent DIC (0.26 mmol, 2.6 eq) was then added, and mixed for 5 minutes. This solution was added to the resin and agitated for 10 minutes. Next, the syringe was placed in a microwave (Emerson 900W Microwave—MW9338SB) set to power level 1 and irradiated for 10 minutes, stopping to shake the syringe every 90 seconds. The syringe was then agitated at RT for an additional 30 minutes. The resin was washed with NMP (×1), DMF (×5), and $CH_2Cl_2$ (×5), and dried in vacuo overnight.

Peptides and glycopeptides also were assembled on a Prelude® Peptide Synthesizer (Protein Technologies, Inc., Tucson, Ariz., USA) using the reaction scheme that follows: Rink resin (100 mg) was placed into the fritted reaction vessels (RVs). Amino acids were dissolved in DMF at 250 mM concentration, HATU at 375 mM, and TMP at 3M. The following steps were performed for coupling: DMF Top Wash (1.5 mL, 2 min mix and drain; ×6), Deprotection (2% DBU/3% piperidine in DMF; 1.5 mL, 4 min mix and drain; 8 min mix and drain), DMF Top Wash (1.5 ml, 2 min mix and drain; ×5), Amino Acid Building Block (0.950 mL, 30 sec mix), Activator 1 (HATU, 0.650 mL, 30 sec mix), Base (TMP, 0.300 mL, 35 min mix and drain), DMF Top Wash (1.5 mL, 2 min mix and drain; ×2). After coupling aspartic acid D7, the deprotection solution was changed to 0.1 M HOBt·H₂O/5% piperazine in DMF to minimize aspartimide formation.

Cleavage of the peptides and glycopeptides from the resin was accomplished with a TFA "cocktail" of $F_3CCOOH$:$Et_3SiH$:$H_2O$:$CH_2Cl_2$:Ph-OCH₃ (by volume, 9:0.3:0.2:1:0.05), agitating at RT for 2 hours. The resulting solutions were expelled into 15 mL centrifuge tubes, evaporated under argon, precipitated in ice-cold $Et_2O$, decanted, and rewashed with $Et_2O$, then dissolved in $H_2O$ and lyophilized to afford the crude material as fluffy white solids.

Purification of the crude glycopeptides was accomplished by Reversed Phase HPLC (RP-HPLC) with a preparative RP (C-18) Phenomenex (250×22 mm) column using a $CH_3CN$—$H_2O$ gradient solvent system containing 0.1% $F_3CCOOH$. Homogeneity of the purified glycopeptides was confirmed by analytical RP-HPLC and high resolution mass spectrometry.

We then tested the neuroprotective effects of the $PAC_1$ agonist and the anti-inflammatory effects of the $VPAC_1$ antagonist in cell culture models and we tested their stability and BBB penetration in vivo. This work sets the stage for studies to test the successful therapeutic candidates in vivo in preclinical models of ALS and PD.

The overall process is as follows: Flow-injection tandem mass spectrometry (FI-MS$^n$) was used to observe the degradation of the peptides and glycopeptides with a Thermo LCQ with electrospray ionization (ESI). The technique involved injection of a sample bolus of material in mouse serum via a six port valve with fluid flow delivered via a syringe pump, and subsequent electrospray ionization (ESI) followed by mass spectral analysis. Samples were diluted to a concentration of ~5 µM of each PACAP analogue, and were incubated at 37° C. for times varying from 1 to 60 minutes. After samples had been incubated for the prescribed amount of time they were prepared for mass spectrometry analysis by withdrawing 10 microliters of solution and spiking with 1 microliter of a 10 µm solution of peptide internal standard (angiotensin II) in 50% acetic acid and subjecting them to a standard C18 zip tip desalting. These solutions, once eluted from the zip tip were diluted to 100 µL in 50:50 acetonitrile/water with 0.1% formic acid. Tandem mass spectrometry analysis ($MS^3$) was conducted to yield specific, quantitative signals proportional to the amount of PACAP analogue at each time point. This technique was also used with microdiasylate samples from a mouse after i.p. administration of PACAP1-27-S-G.

A custom DNA clone of the human PAC1 gene with 3 hemagglutinin (HA) tags inserted 3' to the signal peptide sequence (to avoid proteolytic loss) was obtained from Genecopoeia (Rockville, Md.). The construct was electroporated into Chinese Hamster Ovary (CHO) cells, and selected for with 500 µg/mL of G418. The resulting population was screened for high expressing clones, and one such clone selected for further analysis. The clonal cell line ($PAC_1$-CHO) displayed high receptor expression by immunocytochemistry and Western blot, and showed selective activation of signaling in response to $PACAP_{1-27}$. This cell line was used for all molecular pharmacology experiments. The cells were maintained in DMEM/F12 with 10% heat-inactivated FBS, 1× penicillin/streptomycin, and 500 µg/mL G418, at 37° C. and 5% $CO_2$.

All molecular pharmacology experiments were carried out using a FLIPR Tetra from Molecular Devices (Sunnyvale, Calif.), set to image calcium flux using the manufacturer's recommended settings and protocols. The day before an experiment, the $PAC_1$-CHO cells were split into 384 well black walled, clear bottom microplates, 10,000 cells per well. The cells were recovered overnight in growth medium (as above). The next day, the growth medium was replaced with Calcium 6 dye (Molecular Devices) using the manufacturer recommended buffer with 2.5 mM probenecid. The cells were incubated for 2 hours in the culture incubator, and removed during the last 15 minutes to allow equilibration to room temperature. Compound as indicated below was added to the cells using a 384 tip block, with real time monitoring before, during, and 15 minutes after compound addition. The resulting calcium flux was recorded, and the maximum-minimum response over the entire observation time calculated and reported as the mean±SEM (4 wells per point).

For agonist mode experiments, compound was added in an 11 point concentration curve, with a vehicle control (buffer). The resulting response was normalized to the stimulation caused by $PACAP_{1-27}$ (100%) and vehicle (0%). The response was analyzed using a 3 variable non-linear curve fit, and the $EC_{50}$ (nM) and $E_{Max}$ (%) calculated and reported (Prism, GraphPad, La Jolla, Calif.).

For antagonist mode experiments, a concentration curve (variable concentration mode) or fixed amount (fixed concentration mode) of antagonist was added to the cells, and allowed to equilibrate for 2 minutes. Then, either a 5 nM fixed concentration (variable concentration mode) or an 11 point concentration curve (fixed concentration mode) of $PACAP_{1-27}$ was added to the cells, and the max-min response recorded as above. For variable concentration mode experiments, the data was normalized to the stimulation caused by 5 nM $PACAP_{1-27}$ (100%) and vehicle (0%), and analyzed with a 3 variable non-linear curve fit, with the $IC_{50}$ (nM) and $I_{Max}$ (%) calculated and reported (Prism). For the fixed concentration mode experiments, each curve was normalized to the maximum stimulation caused by $PACAP_{1-27}$ with no antagonist present (100%) and vehicle (0%). The resulting data was analyzed using a Gaddum/Schild $EC_{50}$ shift model, (Schild, 1957, Gaddum, 1957) designed to analyze competitive antagonism. (Lazareno and Birdsall, 1993) The data output was the pA2 (nM) and the Schild Slope, a measure of how closely the experimental data fits the operational model of competitive antagonism (Prism). For all analyses, each independent experiment performed in quadruplicate is considered to be a sample size of 1. The pharmacology values are calculated separately from each experiment, then combined and reported as the mean±SEM for the entire set of experiments.

The PC12 cells were cultured in RPMI containing 5% heat inactivated fetal bovine serum and 10% horse serum in the presence of 100 units/mL penicillin and 100 microgram/mL streptomycin. The cells were plated on poly-D-Lysine coated 6-well tissue culture plates at a density of 150,000 cells per well in 2 mL media. After 48 hours at 37° C. in 5% $CO_2$ atmosphere, media exchange was performed and plates were dosed, using the peptide diluent (water) for the control samples. $PACAP_{1-27}$, $PACAP_{1-27-S-G}$, and $PACAP_{1-27-S-L}$ were used to screen for $PAC_1$ receptor activation. Four groups of cells were used; one control group (diluent treated) and three treatment groups, each treatment group was exposed to 100 nM concentrations of $PACAP_{1-27}$, $PACAP_{1-27-S-G}$, or $PACAP_{1-27-S-L}$. All groups were run in triplicate. Cell images of each treatment group were captured and compared to the control cells to screen for differentiation and cell body volume increases. Cells having neurite-like process outgrowth were noted and photographed. The neurite-like outgrowth was deemed positive if its length was at least two times the width of the cell body.

Results

PACAP derivatives and glycosides were synthesized on a small scale (~5 mg) using prior art solid-phase methods previously described[26, 27]. Recent advances in the synthesis of Fmoc-protected glycosides of Serine and Threonine using "minimally competent" Lewis acid promoters allows us to produce the required glycosides in high yield and purity[28], which in turn provides the O-linked glycopeptides[29].

FIG. 1 is a molecular dynamics representation (MOE®) of $PACAP_{1-27}$ that has been modified by replacing the terminal Leucine 27 amide with a Serine lactoside amide (Ser-O-β-D-Glc-β-D-Gal). The calculations suggest that the PACAP glycosides can adopt a largely helical conformation.

TABLE 1

Representative analogs of PACAP

| Peptides\Glycopeptides | Amino Acid Sequence (C-Terminal Amides) |
| --- | --- |
| $PACAP_{1-27}$ | HSDGIFTDSYSRYRKQMAVKKY LAAVL (SEQ ID NO:3) |
| $PACAP_{1-27-S-G}$ | HSDGIFTDSY$_{10}$SRYRKQMAVK$_{20}$KY LAAVS-O-β-D-Glc (SEQ ID NO:4) |
| $PACAP_{6-27}$ | FTDSY$_{10}$SRYRKQMAVK$_{20}$KYLAAVL (SEQ ID NO:5) |
| $PACAP_{6-38}$ | FTDSY$_{10}$SRYRKQMAVK$_{20}$KYLAAVL GKR$_{30}$YKQRVKNY (SEQ ID NO:6) |
| $PACAP_{6-27-S-G}$ | FTDSY$_{10}$SRYRKQMAVK$_{20}$KYLAAVS-O-β-D-Glc (SEQ ID NO:7) |
| $PACAP_{6-27-S-L}$ | FTDSY$_{10}$SRYRKQMAVK$_{20}$KYLAAVS-O-β-D-Glc-β-D-Gal(SEQ ID NO:8) |
| $PACAP_{6-27-Alt}$ | FTDSY$_{10}$SRYRRQLAVR$_{20}$RYLAAVL (SEQ ID NO:9) |
| $PACAP_{6-27-S-G-Alt}$ | FTDSY$_{10}$SRYRRQLAVR$_{20}$RYLAAVS-O-β-D-Glc (SEQ ID NO:10) |
| $PACAP_{6-27-S-L-Alt}$ | FTDSY$_{10}$SRYRRQLAVR$_{20}$RYLAAVS-O-β-D-Glc-β-D-Gal (SEQ ID NO:11) |

The truncated peptides and glycopeptides are missing five N-terminal amino acids responsible for binding to the transmembrane portion of the GPCR receptors and were expected to be antagonists. For the glycosides Leucine 27 has been replaced (underlined residues) by a Serine glycoside bearing glucose (-β-D-Glc) or lactose (-β-D-Glc-β-D-Gal). The final 3 alternate compounds have been modified by replacing methionine 17 with Leucine, and Lysines 15, 20 and 21 with Arginines to enhance stability in vivo, and were expected to be antagonists at $PAC_1$.

Chemical stability of the glycopeptides in vivo clearly plays an important role in the deliverability of the drugs to the site(s) of action within the brain. It is also important to know what the chemical or metabolic instabilities are in order to inform the drug design process. Tandem mass spectroscopy ($MS^n$) was used to determine both the stability of the PACAP compounds in mouse serum, and to identify specific cleavage products, which can stem from inherent chemical instability, or from enzymatic hydrolysis.

Figure 2:
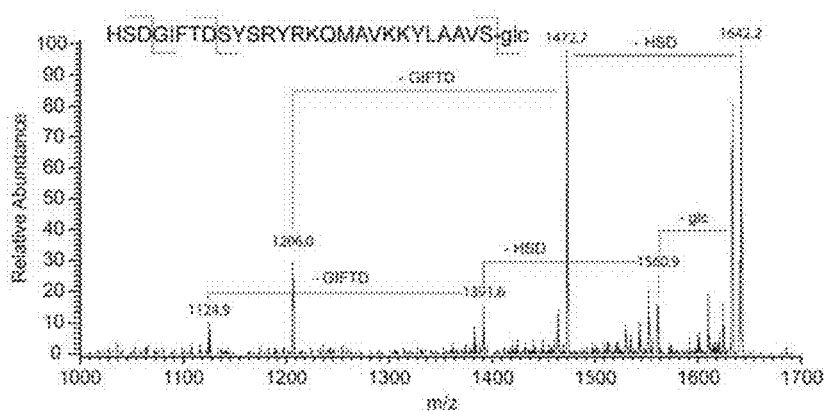
FIG. 2 shows MS fragmentation of glucoside $PACAP_{1-27-S-G}$ in accordance with the present invention.

Collision induced fragmentation of the $2^+$ ion at 1642.7 m/z from mouse brain dialysate carried out using MS/MS. This spectrum (see FIG. 2) shows a clear pattern from the N-terminus in which fragmentation occurs at the aspartic acid residues resulting $y^{2+}$ ions. The glycosylated $y_{19}^{2+}$ and $y_{24}^{2+}$ at 1206.0 and 1472.7 m/z respectively, are the predominant ions in the spectrum ($NH_3$ loss omitted for clarity). β-Glc cleavage gave 1560.9 m/z, matching the calculated mass for $PACAP_{1-27}$ with a C-terminal amide. Loss of the glucoside along with peptide backbone cleavage resulted in $y_{19}^{2+}$ and $y_{24}^{2+}$ ions at 1124.9 and m/z 1391.6.

Stability of $PACAP_{1-27}$; $PACAP_{1-27-S-G}$ and $PACAP_{1-27-S-L}$ was tested. FIG. 3 shows that $PACAP_{1-27}$ and its glycosylated analogues degraded over 30 min in mouse serum at 37° C., as revealed by "shotgun" $FI-MS^n$ analysis. Data were fitted using a single exponential decay model ($R^2 > 0.71$, in all cases). FIG. 4 shows that Serine glucoside ($PACAP_{1-27-S-G}$, Glc) showed a significant increase in mouse serum $t_{1/2}$ in vitro compared to the native peptide $PACAP_{1-27}$ and the corresponding lactoside ($PACAP_{1-27-S-L}$, Lac) when compared using a 1-way analysis of variance (F2=12.91, p=0.0067, Tukey's multiple comparison Native vs Glc, q=5.760 p<0.05, Lac vs Glc, q=6.602 p<0.5). FIG. 5 shows that $CLC-MS^3$ allowed for rapid separation and simultaneous quantification of Native, Glc, and Lac PACAP derivatives. The $MS^2$ fragmentation pattern ($MS^2$ spectrum) for native PACAP, and the fragmentation patterns ($MS^3$ spectra) of Glc and Lac are shown. Interestingly, all resulted in the same primary fragment ion at 755 m/z. The specific ion transitions observed: $PACAP_{1-27}$ Native 630→755, $PACAP_{1-27-S-G}$, Glc 657→625→755, $PACAP_{1-27-S-L}$ Lac 690→625→755.

Using CHO cells that express human $PAC_1$ receptors, we tested $PACAP_{1-27}$, the glucoside $PACAP_{27-S-G}$, and the truncated putative antagonist $PACAP_{6-27}$ and its derivatives as agonists using FLIPR. We found that $PACAP_{1-27}$ and $PACAP_{1-27-S-G}$, the serine glucoside, activated $PAC_1$ with high potency (0.95±0.4 nM and 5.68±2.3 nM respectively, FIG. 6 and Table 2). These values are both very similar to what has been reported for $PACAP_{1-27}$. In addition, the normalized efficacy of the $PACAP_{1-27-S-G}$ glucoside was nearly identical to the native $PACAP_{1-27}$ peptide, at 101.9±1.6%. These findings strongly suggest that glycosylation of $PACAP_{1-27}$ does not significantly alter binding and activation of the $PAC_1$ receptor, supporting the use of such a glycopeptide for therapeutic purposes. As expected, none of the $PACAP_{6-27}$ derivatives showed agonist activity at concentrations up to 1 μM (FIG. 6 and Table 2).

$PAC_1$-CHO calcium flux activation was measured using FLIPR in response to 11 point concentration curves of $PACAP_{1-27}$, the glucoside $PACAP_{1-27-S-G}$, and the truncated derivatives (putative antagonists) of $PACAP_{6-27}$. Response was measured over 10 minutes, the max-min calculated, and all data was normalized to the maximum response caused by $PACAP_{1-27}$ (100%) and vehicle (0%). The mean±SEM is shown, using the mean value from each independent experiment. N=3 independent experiments performed, 3 variable non-linear curve fit using Prism. Derived values reported in Table 2. $PACAP_{1-27}$ and $PACAP_{1-27-S-G}$ display potent, efficacious agonist activity.

In addition to the agonist studies above, we also tested the ability of glycosylated and non-glycosylated $PACAP_{6-27}$ derivatives to block activation of the $PAC_1$ receptor by $PACAP_{1-27}$. We first used a variable concentration mode antagonist assay versus 5 nM of $PACAP_{1-27}$ in the $PAC_1$-CHO cells using FLIPR. Surprisingly, we could detect no antagonist activity of $PACAP_{6-27}$ or any derivative up to 1 μM (FIG. 7A-C and Table 2). In addition, we tested the known antagonist $PACAP_{6-38}$, and could only detect low potency antagonism (>333 nM, FIG. 7A and Table 2). These findings are at odds with a molecular pharmacology study of $PACAP_{6-38}$ and $PACAP_{6-27}$ with reported $K_i$ values of 1.5 and 60 nM, respectively by Robberecht et al.[30].

The ability of $PACAP_{6-27}$ derivatives to block $PACAP_{1-27}$ induced calcium flux was measured using FLIPR. Derived values are reported in Table 2. FIG. 7A shows variable concentration mode antagonist experiments. Concentration curves of $PACAP_{6-38}$, $PACAP_{6-27}$, and $PACAP_{6-27}$ derivatives were added to the cells for 2 minutes, followed by 5 nM of $PACAP_{1-27}$. The max-min response was determined, and normalized to the stimulation caused by 5 nM $PACAP_{1-27}$ (100%) and vehicle (0%). 3 variable non-linear curve fit (Prism), N=3-4 independent experiments, mean±SEM reported. Only $PACAP_{6-38}$ shows antagonism, but it is low potency. FIG. 7B shows fixed concentration mode experiments with $PACAP_{6-38}$. Fixed concentrations of $PACAP_{6-38}$ added to cells for 2 minutes, followed by concentration curves of $PACAP_{1-27}$. The max-min response was determined, and normalized to the max response of the $PACAP_{1-27}$ curve without antagonist present (100%) and vehicle (0%). Gaddum/Schild $EC_{50}$ Shift model (Prism), N=3 independent experiments. $PACAP_{6-38}$ shifts the curve only at the highest concentration (1 μM). FIG. 7C shows fixed concentration mode experiments with $PACAP_{6-27}$, performed as in FIG. 7B N=3 independent experiments. $PACAP_{6-27}$ showed no detectable shifts in the agonist curves.

However, one further difference with reported values[30] remained, which was the use of fixed concentration antagonist mode experiments. This mode is the most sensitive means of detecting antagonist activity, so we performed experiments using this method with the peptides $PACAP_{6-27}$ and $PACAP_{6-38}$. We found that $PACAP_{6-27}$ caused no shift in the agonist curves, while $PACAP_{6-38}$ induced a shift only at 1 μM (FIGS. 7B, 7C and Table 2). This resulted in a pA2 value of 200.6±55.4 nM for $PACAP_{6-38}$, again well above the 1.5 nM value previously reported[30]. Notably, $PACAP_{6-38}$ also showed a Schild Slope of 2.0±0.1. A Schild Slope of 1 fits the assumptions of the model, while a slope above 1 suggests that the compound is more effective than would be expected for competitive antagonism. This could be due to the short incubation times in the FLIPR assay, which might not be long enough to allow the system to reach equilibrium. The model is only valid at equilibrium. This would result in a high Schild Slope. Alternatively, $PACAP_{6-38}$ could function by a different mechanism, e.g. binding to $VPAC_{1/2}$.

TABLE 2

Agonist Data

| Compound | EC$_{50}$ (nM) | E$_{Max}$ (%) |
|---|---|---|
| PACAP1-27 | 0.95 ± 0.4 | 100 |
| PACAP1-27-S-G | 5.68 ± 2.3 | 101.9 ± 1.6 |
| PACAP6-27 | NC | |
| PACAP6-27-S-G | NC | |
| PACAP6-27-S-L | NC | |
| PACAP6-27-Alt | NC | |
| PACAP6-27-S-G-Alt | NC | |
| PACAP6-27-S-L-Alt | NC | |

Antagonist Data (Variable Concentration)

| Compound | IC$_{50}$ (nM) | I$_{Max}$ (%) |
|---|---|---|
| PACAP6-38 | >333 | (78.8) |
| PACAP6-27 | NC | |
| PACAP6-27-S-G | NC | |
| PACAP6-27-S-L | NC | |
| PACAP6-27-Alt | NC | |
| PACAP6-27-S-G-Alt | NC | |
| PACAP6-27-S-L-Alt | NC | |

Antagonist Data (Fixed Concentration)

| Compound | pA2 (nM) | Schild Slope |
|---|---|---|
| PACAP6-38 | 200.6 ± 55.4 | 2.0 ± 0.1 |
| PACAP6-27 | NC | |

Mean values±SEM reported, derived from the curves in FIGS. 6 and 7. N=3-4 independent experiments. One experiment for PACAP$_{6-38}$ in the Fixed Concentration set could not be fitted to the curves, so N=2 for those values (N=3 for curves in FIGS. 7A-C). NC=not converged, no curves could be fit or activity detected. ( )=% inhibition at highest concentration since the curve bottom could not be reliably fit.

PC12 cells are non-adherent cells, and in spite of using the poly-D-Lysine coated plates, the majority of the cells remained suspended. During the media exchange many of the cells were removed with the spent media. The remaining cells could be visually evaluated for qualitative morphological changes at the end of the treatment period, but meaningful cell quantification could not be done reliably using this approach. We found that glucoside and lactoside PACAP$_{1-27}$ derivative treatment produced neurite outgrowth and arborization when compared to vehicle treated cells (FIGS. 8A-D). Qualitatively, it appeared that the arborization caused by PACAP$_{1-27}$ may be more extensive than that caused by the glucoside and lactoside derivatives, but again this could not be quantified. In any case, both PACAP$_{1-27}$ and the derivatives induced neurite outgrowth, suggesting native PAC$_1$ agonist activity.

Figure 8A:
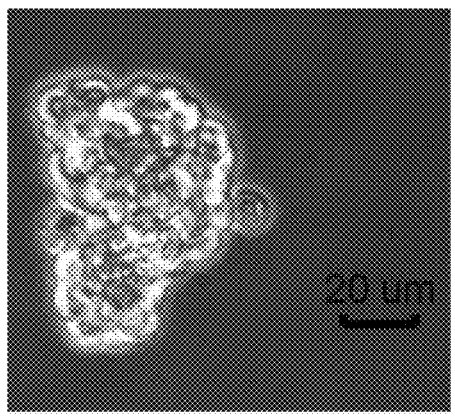
Figure 8B:
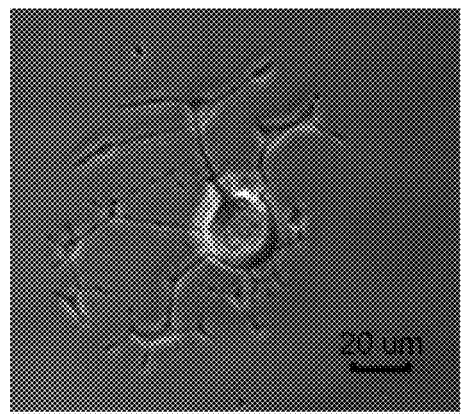
Figure 8C:
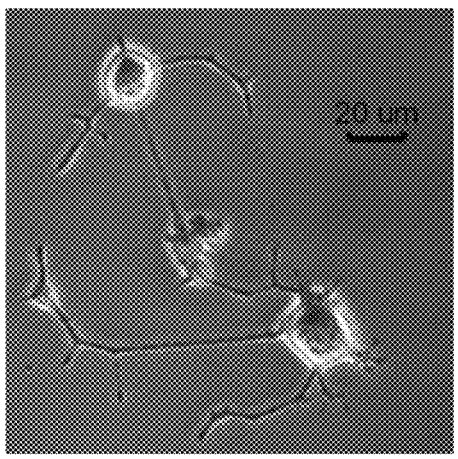
Figure 8D:
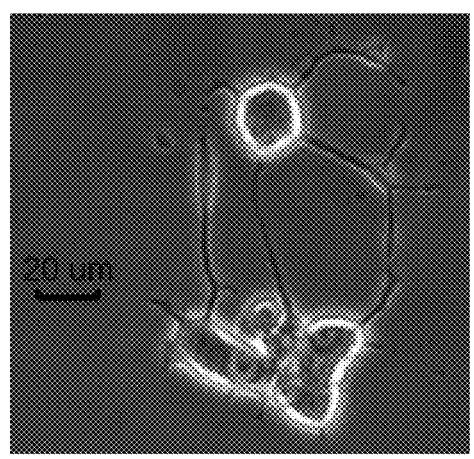

FIGS. 8A-8D show PC12 Cell Morphology after Vehicle vs PACAP Treatment (100 nM). FIG. 8A: diluent only. FIG. 8B: PACAP$_{1-27}$, FIG. 8C: PACAP$_{1-27-S-G}$, FIG. 8D: PACAP$_{1-27-S-L}$. The cell body volumes all showed increases when treated with each of the PACAP derivatives in Table 1. In all cases the process outgrowths on the treated cells were greater than 2× the cell body width Endogenous PACAP peptides occur as C-terminal peptide amides that have either 27 (10%) or 38 (90%) amino acid residues, and are typically regarded as PAC$_1$ agonists in assays using intact tissue or in cell culture. For the present studies we have developed a separate CHO cell line expressing the PAC$_1$ receptor individually. Use of solid-phase peptide synthesis has allowed us to replace the terminal Leucine amide with glycosides of Serine amide bearing the simple sugars glucose or lactose. We were gratified to see that these O-linked glycopeptides not only retained their agonist activity on PC12 cell cultures (FIG. 8) and in the quantitative CHO cell assay (FIG. 6 and Table 2), but also showed extended lifetimes in mouse serum (FIGS. 5A-5C), and provided evidence via microdialysis studies that the glycopeptides can cross the blood brain barrier in mice (FIGS. 5A-5C). In use, an effective amount of the PACAP-VIP glycopeptides of the present invention may be administered to a patient in need of treatment in a therapeutically effective unit dose delivery amount of between about 0.1 and 10 milligrams per kilo, typically 1-2 doses per day, or even less frequently. The PACAP-VIP glycopeptides may be delivered in a pharmaceutically acceptable carrier.

Pharmaceutical formulations and pharmaceutical compositions are well known in the art, and can be found, for example, in Remington's Pharmaceutical Sciences, Mack Publishing Co., Easton, Pa., USA, which is hereby incorporated by reference in its entirety. Any formulations described therein or otherwise known in the art are embraced by embodiments of the disclosure.

Pharmaceutical excipients are well known in the art and include, but are not limited to, saccharides such as, for example, lactose or sucrose, mannitol or sorbitol, cellulose preparations, calcium phosphates such as tricalcium phosphate or calcium hydrogen phosphate, as well as binders, such as, starch paste such as, for example, maize starch, wheat starch, rice starch, potato starch, gelatin, tragacanth, methyl cellulose, hydroxypropylmethylcellulose, sodium carboxymethylcellulose, polyvinyl pyrrolidone or combinations thereof.

In particular embodiments, pharmaceutical formulations may include the active compound described and embodied above, a pharmaceutically acceptable carrier or excipient and any number of additional or auxiliary components known in the pharmaceutical arts such as, for example, binders, fillers, disintegrating agents, sweeteners, wetting agents, colorants, sustained release agents, and the like, and in certain embodiments, the pharmaceutical composition may include one or more secondary active agents. Disintegrating agents, such as starches as described above, carboxymethyl-starch, cross-linked polyvinyl pyrrolidone, agar, alginic acid or a salt thereof, such as sodium alginate and combinations thereof. Auxiliary agents may include, for example, flow-regulating agents and lubricants, such as silica, talc, stearic acid or salts thereof, such as magnesium stearate or calcium stearate, polyethylene glycol and combinations thereof. In certain embodiments, dragee cores may be prepared with suitable coatings that are resistant to gastric juices, such as concentrated saccharide solutions, which may contain, for example, gum arabic, talc, polyvinyl pyrrolidone, polyethylene glycol, titanium dioxide, lacquer solutions and suitable organic solvents or solvent mixtures and combinations thereof. In order to produce coatings resistant to gastric juices, solutions of suitable cellulose preparations, such as acetylcellulose phthalate or hydroxypropylmethylcellulose phthalate may also be used. In still other embodiments, dye stuffs or pigments may be added to the tablets or dragee coatings, for example, for identification or in order to characterize combinations of active compound doses.

Pharmaceutical compositions of the disclosure can be administered to any animal, and in particular, any mammal, that may experience a beneficial effect as a result of being administered a compound of the disclosure including, but not limited to, humans, canines, felines, livestock, horses, cattle, sheep, and the like. The dosage or amount of at least one compound according to the disclosure provided pharmaceutical compositions of embodiments may vary and may depend, for example, on the use of the pharmaceutical composition, the mode of administration or delivery of the pharmaceutical composition, the disease indication being treated, the age, health, weight, etc. of the recipient, concurrent treatment, if any, frequency of treatment, and the nature of the effect desired and so on. Various embodiments of the disclosure include pharmaceutical compositions that include one or more compounds of the disclosure in an amount sufficient to treat or prevent diseases such as, for example, cancer. An effective amount of the one or more compounds may vary and may be, for example, from about 0.1 to 10 milligrams per kilo, typically 1-2 doses per day.

The pharmaceutical compositions of the disclosure can be administered by any means that achieve their intended purpose. For example, routes of administration encompassed by the disclosure include, but are not limited to, subcutaneous, intravenous, intramuscular, intraperitoneal, buccal, or ocular routes, rectally, parenterally, intrasystemically, intravaginally, topically (as by powders, ointments, drops or transdermal patch), oral or nasal spray are contemplated in combination with the above described compositions.

Embodiments of the disclosure also include methods for preparing pharmaceutical compositions as described above by, for example, conventional mixing, granulating, dragee-making, dissolving, lyophilizing processes and the like. For example, pharmaceutical compositions for oral use can be obtained by combining the one or more active compounds with one or more solid excipients and, optionally, grinding the mixture.

Suitable auxiliaries may then be added and the mixture may be processed to form granules which may be used to form tablets or dragee cores. Other pharmaceutical solid preparations include push-fit capsules containing granules of one or more compound of the disclosure that can, in some embodiments, be mixed, for example, with fillers, binders, lubricants, stearate, stabilizers or combinations thereof. Push-fit capsules are well known and may be made of gelatin alone or gelatin in combination with one or more plasticizer such as glycerol or sorbitol to form a soft capsule. In embodiments in which soft capsules are utilized, compounds of the disclosure may be dissolved or suspended in one or more suitable liquids, such as, fatty oils or liquid paraffin and, in some cases, one or more stabilizers.

Liquid dosage formulations suitable for oral administration are also encompassed by embodiments of the disclosure. Such embodiments, may include one or more compounds of the disclosure in pharmaceutically acceptable emulsions, solutions, suspensions, syrups, and elixirs that may contain, for example, one or more inert diluents commonly used in the art such as, but not limited to, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (for example, cottonseed, groundnut, corn, germ, olive, castor, and sesame oils), glycerol, fatty acid derivatives of glycerol (for example, labrasol), tetrahydrofurfuryl alcohol, polyethylene glycols and fatty acid esters of sorbitan, and mixtures thereof. Suspensions may further contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Formulations for parenteral administration may include one or more compounds of the disclosure in water-soluble form, for example, water-soluble salts, alkaline solutions, and cyclodextrin inclusion complexes in a physiologically acceptable diluent which may be administered by injection. Physiologically acceptable diluent of such embodiments, may include, for example, sterile liquids such as water, saline, aqueous dextrose, other pharmaceutically acceptable sugar solutions; alcohols such as ethanol, isopropanol or hexadecyl alcohol; glycols such as propylene glycol or polyethylene glycol; glycerol ketals such as 2,2-dimethyl-1,3-dioxolane-4-methanol; ethers such as poly(ethyleneglycol)400; pharmaceutically acceptable oils such as fatty acid, fatty acid ester or glyceride, or an acetylated fatty acid glyceride. In some embodiments, formulations suitable for parenteral administration may additionally include one or more pharmaceutically acceptable surfactants, such as a soap or detergent; suspending agent such as pectin, carbomers, methylcellulose, hydroxypropylmethylcellulose, or carboxymethylcellulose; an emulsifying agent; pharmaceutically acceptable adjuvants or combinations thereof. Additional pharmaceutically acceptable oils which may be useful in such formulations include those of petroleum, animal, vegetable or synthetic origin including, but not limited to, peanut oil, soybean oil, sesame oil, cottonseed oil, olive oil, sunflower oil, petrolatum, and mineral oil; fatty acids such as oleic acid, stearic acid, and isostearic acid; and fatty acid esters such as ethyl oleate and isopropyl myristate. Additional suitable detergents include, for example, fatty acid alkali metal, ammonium, and triethanolamine salts; cationic detergents such as dimethyl dialkyl ammonium halides, alkyl pyridinium halides, and alkylamine acetates; and anionic detergents, such as alkyl, aryl, and olefin sulfonates, alkyl, olefin, ether and monoglyceride sulfates, and sulfosuccinates. In some embodiments, non-ionic detergents including, but not limited to, fatty amine oxides, fatty acid alkanolamides and polyoxyethylenepolypropylene copolymers or amphoteric detergents such as alkyl-β-aminopropionates and 2-alkylimidazoline quaternary salts, and mixtures thereof may be useful in parenteral formulations of the disclosure.

Pharmaceutical compositions for parenteral administration may contain from about 0.5 to about 25% by weight of one or more of the compounds of the disclosure and from about 0.05% to about 5% suspending agent in an isotonic medium. In various embodiments, the injectable solution should be sterile and should be fluid to the extent that it can be easily loaded into a syringe. In addition, injectable pharmaceutical compositions may be stable under the conditions of manufacture and storage and may be preserved against the contaminating action of microorganisms such as bacteria and fungi.

Topical administration includes administration to the skin or mucosa, including surfaces of the lung and eye. Compositions for topical administration, may be prepared as a dry powder which may be pressurized or non-pressurized. In non-pressurized powder compositions, the active ingredients in admixture are prepared as a finely divided powder. In such embodiments, at least 95% by weight of the particles of the admixture may have an effective particle size in the range of 0.01 to 10 micrometers. In some embodiments, the finely divided admixture powder may be additionally mixed with an inert carrier such as a sugar having a larger particle size, for example, of up to 100 micrometers in diameter. Alternatively, the composition may be pressurized using a compressed gas, such as nitrogen or a liquefied gas propellant. In embodiments, in which a liquefied propellant medium is used, the propellant may be chosen such that the compound and/or an admixture including the compound do not dissolve in the propellant to any substantial extent. In some embodiments, a pressurized form of the composition may also contain a surface-active agent. The surface-active agent may be a liquid or solid non-ionic surface-active agent or may be a solid anionic surface-active agent, which in certain embodiments, may be in the form of a sodium salt.

Compositions for rectal administration may be prepared by mixing the compounds or compositions of the disclosure with suitable non-irritating excipients or carriers such as for example, cocoa butter, polyethylene glycol or a suppository wax. Such carriers may be solid at room temperature but liquid at body temperature and therefore melt in the rectum and release the drugs.

In still other embodiments, the compounds or compositions of the disclosure can be administered in the form of liposomes. Liposomes are generally derived from phospholipids or other lipid substances that form mono- or multi-lamellar hydrated liquid crystals when dispersed in an aqueous medium. Any non-toxic, physiologically acceptable and metabolizable lipid capable of forming liposomes can be used, and in particular embodiments, the lipids utilized may be natural and/or synthetic phospholipids and phosphatidyl cholines (lecithins). Methods to form liposomes are known in the art (see, for example, Prescott, Ed., Meth. Cell Biol. 14:33 (1976), which is hereby incorporated by reference in its entirety). Compositions including one or more compounds of the disclosure in liposome form can contain, for example, stabilizers, preservatives, excipients and the like.

In general, methods of embodiments of the disclosure may include the step of administering or providing an "effective amount" or a "therapeutically effective amount" of a compound or composition of the disclosure to an individual. In such embodiments, an effective amount of the compounds of the disclosure may be any amount that produces the desired effect. As described above, this amount may vary depending on, for example, the circumstances under which the compound or composition is administered (e.g., to incite treatment or prophylactically), the type of individual, the size, health, etc. of the individual and so on. The dosage may further vary based on the severity of the condition. For example, a higher dose may be administered to treat an individual with a well-developed metastatic condition, compared to the amount used to prevent a subject from developing the metastatic condition. Those skilled in the art can discern the proper dosage based on such factors. For example, in some embodiments, the dosage may be within the range of about 0.01 mg/kg body weight to about 10 mg/kg body weight.

The administration schedule may also vary. For example, in some embodiments, the compounds or compositions of the disclosure may be administered in a single dose once per day or once per week. In other embodiments, the compounds or compositions of the disclosure may be administered in one or two or more doses per day. For example, in one embodiment, an effective amount for a single day may be divided into separate dosages that may contain the same or a different amount of the compound or composition and may be administered several times throughout a single day. Without wishing to be bound by theory, the dosage per administration and frequency of administration may depend, for example, on the specific compound or composition used, the condition being treated, the severity of the condition being treated, and the age, weight, and general physical condition of the individual to which the compound or composition is administered and other medications which the individual may be taking. In another exemplary embodiment, treatment may be initiated with smaller dosages that are less than the optimum dose of the compound, and the dosage may be increased incrementally until a more optimum dosage is achieved.

In each of the embodiments above, the compound administered can be provided as a pharmaceutical composition including compound as described above and a pharmaceutically acceptable excipient or a pure form of the compound may be administered.

In additional embodiments, the compound or composition of the disclosure may be used alone or in combination with one or more additional agents. For example, in some embodiments, a compound or composition of disclosure may be formulated with one or more additional anti-cancer agents or combinations thereof such that the pharmaceutical composition obtained including the compound or composition of the disclosure and the one or more additional agents can be delivered to an individual in a single dose. In other embodiments, the compound or composition of the disclosure may be formulated as a separate pharmaceutical composition that is delivered in a separate dose from pharmaceutical compositions including the one or more additional agents. In such embodiments, two or more pharmaceutical compositions may be administered to deliver effective amounts of a compound or composition of the disclosure and the one or more additional agents.

The results of the study strongly support the notion that glycopeptides related to PACAP produce $PAC_1$ agonism, or $VPAC_1$ agonism or $VPAC_2$ agonism, all of which may be useful feature for the treatment of neurodegeneration, particularly for PD. In addition, $VPAC_1$ antagonism or $VPAC_2$ antagonism combined with $PAC_1$ agonism may be particularly effective.

Our results also show that glycosylation of PACAP peptides is a good strategy for increasing the in vivo stability and CNS penetration of peptide drugs, which may be useful as a strategy for the treatment of diseases like PD migraine, traumatic brain injury and stroke.

The PACAP-VIP glycopeptides of the present invention have several significant advantages.
1. By only binding $PAC_1$ and VPAC receptors and nothing else, the protein has a very narrow range of influence. Side effects therefore, are at a minimum.
2. The protein itself is a variant on an endogenous protein, PACAP. This both allows the protein to cross the blood-brain barrier and diminishes potential immune response, allowing the protein to carry out its function.
3. The invention treats one of the causes of ALS, PD, AD, HD migraines, traumatic brain injury, stroke and forms of dementia rather than just treating symptoms. Thus, the protein has stronger effects than symptom-treating drugs.

Various changes may be made in the above disclosure without departing from the spirit and scope thereof.

REFERENCES

1. McNally, G. P.; Akil, H. Opioid peptides and their receptors: overview and function in pain modulation. In Neuropsychopharmacology: the Fifth Generation of Progress, Davis, K. L.; Charney, D.; Coyle, J. T.; Nemeroff, C. Eds, Lippincott Williams & Wilkins, Philadelphia, 2002, Chapter 3, pp. 35-46.
2. Adessi, C.; Soto, C. Cur. Med. Chem. 2002, 9, 963-978.

3. Reese, T. S.; Karnovsky, M. J. J. Cell. Biol. 1967, 34, 207-217.
4. Pardridge, W. M. Introduction to the Blood-Brain Barrier, Cambridge University Press: New York, 1993.
5. Breig, N. H.; Fredericks, W. R.; Holoway, H. W.; Soncrant, T. T.; Rapoport, S. I. J. Pharmacol. Exp. Ther. 1988, 245, 581-586.
6. a) Hruby, V. J.; Mosberg, H. I. Peptides 1982, 3, 329-336.
   b) Mosberg, H. I., Hurst, R., Hruby, V. J.; Galligan, J. J.; Burks, T. F.; Gee, K.; Yamamura, H. I. Biochem. Biophys. Res. Commun. 1982, 106, 506-512.
7. Hruby, V. J. Biopolymers 1993, 33, 1073-1082.
8. a) Bodor, N.; Prokai, L.; Wu, W. M.; Farag, H.; Jonalagadda, S.; Kawamura, M.; Simpkins, J. Science 1992, 257, 1698-1700.
   b) Rousselle, C.; Clair, P.; Lefauconnier, J. M.; Kaczorek, M.; Scherrmann, J. M.; Temsamani, J. Mol. Pharmacol. 2000, 57, 679-686.
9. a) Albert, R.; Marbach, P.; Bauer, W.; Briner, U.; Fricker, G.; Bruns, C.; Pless, J. Life Sci. 1993, 53, 517-525.
   b) Polt, R.; Porreca, F.; Szabo, L. Z.; Bilsky, E. J.; Davis, P.; Abbruscato, T. J.; Davis, T. P.; Harvath, R.; Yamamura, H. I.; Hruby, V. J. Proc. Natl. Acad. Sci. USA 1994, 91, 7114-7118.
   c) Negri, L.; Lattanzi, R.; Tabacco, F.; Orru, L.; Severini, C.; Scolaro, B.; Rocchi, R. J. Med. Chem. 1999, 42, 400-404. d) Tomatis, R.; Marastoni, M.; Balboni, G.; Guerrini, R.; Capasso, A.; Sorrentino, L.; Santagada, V.; Caliendo, G.; Lazarus, L. H.; Salvadori, S. J. Med. Chem. 1997, 40, 2948-52.
10. a) Egleton, R. D.; Mitchell, S. A.; Huber, J. D.; Palian, M. M.; Polt, R.; Davis, T. P. J. Pharmacol. Exp. Ther. 2001, 299, 967-972.
    b) Bilsky, E. J.; Egleton, R. D.; Mitchell, S. A.; Palian, M. M.; Davis, P. Huber, J. D.; Jones, H.; Yamamura, H. I.; Janders, J.; Davis, T. P.; Porreca, F.; Hruby, V. J.; Polt. R. J. Med. Chem. 2000, 43, 2586-2590.
    c) Elmagbari, N. O.; Egleton, R. D.; Palian, M. M.; Lowery, J. J.; Schmid, W. R.; Davis, P.; Navratilova, E.; Dhanasekaran, M.; Keyari, C. M.; Yamamura, H. I.; Porreca, F.; Hruby, V. J.; Polt, R.; Bilsky, E. J. J. Pharmacol. Expt. Ther. 2004, 311, 290-297.
11. Palian, M. M.; Boguslaysky, V. I.; O'Brien, D. F.; Polt, R. J. Am. Chem. Soc. 2003, 125, 5823-5831.
12. a) Susaki, H.; Suzuki, K.; Yamada, H.; Okuno, S.; Watanabe, H. K. Biol. Pharm. Bull. 1999, 22, 1094-1098.
    b) Suzuki, K.; Susaki, H.; Okuno, S.; Sugiyama, Y. J. Pharmacol. Exp. Ther. 1999, 288, 57-64.
    c) Suzuki, K., Susaki, H.; Okuno, S.; Yamada, H.; Watanabe, H. K.; Sugiyama, Y. J. Pharmacol. Exp. Ther. 1999, 288, 888-897.
13. Egleton, R. D.; Mitchell, S. A.; Huber, J. D.; Janders, J.; Stropova, D.; Polt, R.; Yamamura, H. I.; Hruby, V. J.; Davis, T. P. Brain Res. 2000, 881, 37-46.
14. a) Gysin, B.; Schwyzer, R. Arch. Biochem. Biophys. 1983, 225, 467-474.
15. Lee, N. M.; Smith, A. P. Life Sci. 1980, 26, 1459.
16. Graf, L.; Cseh, C.; Barat, E.; Ronai, A. Z; Szekely, J.; Kennesey, A.; Bajusz, S. Ann. N.Y. Acad. Sci. 1977, 297, 63.
17. Schwyzer, R. Biochemistry 1986, 25, 6336-6342.
18. Taylor, J. W.; Osterman, D. G.; Miller, R. J.; Kaiser, E. T. J. Am. Chem. Soc., 1981, 103, 6965-6966.
19. a) Taylor, J. W.; Kaiser, E. T.; Int. J. Pept. Protein Res. 1989, 34, 75-80.
    b) Blanc, J. P.; Taylor, J. W.; Miller, R. J.; Kaiser, E. T. J. Biol. Chem. 1983, 258, 8277-8284. c) Taylor, J. W.; Miller, R. J.; Kaiser, E. T. J. Biol. Chem. 1983, 258, 4464-4471.
20. a) Taylor, J. W.; Miller, R. J.; Kaiser, E. T. Mol. Pharmacol. 1982, 22, 657-666.
    b) Taylor, J. W.; Kaiser, E. T. Methods Enzymol. 1987, 154, 473-499.
21. Goldstein, A.; Fischli, W.; Lowney, L. I.; Hunkapiller, M.; Hood, L. Proc. Natl. Acad. Sci. USA. 1981, 78, 7219-7223.
22. Chavkin, C.; Goldstein, A. Proc. Natl. Acad. Sci. USA. 1981, 78, 6543-6547.
23. a) Renugopalakrishnan, V.; Rapaka, R. S.; Huang, S.-G.; Moore, S.; Houston, T. B. Biochem. Biophys. Res. Commun. 1988, 151, 1220-1225.
    b) Zhou, N.; Gibbons, W. A. J. Chem. Soc., Perkin Trans. 1986, 2, 637-644.
    c) Maroun, R.; Mattice, W. L. Biochem. Biophys. Res. Commun. 1981, 103, 442-446.
    d) Spadaccini, R.; Crescenzi, O.; Picone, D.; Tancredi, T.; Temussi, A. J. Peptide Sci. 1999, 5, 306-312.
24. Tessmer, M.; Kallick, D. A. Biochemistry 1997, 36, 1971-1981.
25. a) Luna, F-D. T.; Collins, N.; Stropova, D.; Davis, P.; Yamamura, H. I.; Porreca, F.; Hruby, V. J. J. Med. Chem. 1996, 39, 1136-1141.
26. Polt, R.; Szabò, L. Z.; Treiberg, J.; Li, Y.; Hruby, V. J. (1992) General Methods for α- or β-O-Ser/Thr Glycosides and Glycopeptides. Solid-Phase Synthesis of 0-Glycosyl Cyclic Enkephalin Analogues. J. Am. Chem. Soc. 114, 10249-10258.
27. Mitchell, S. A.; Pratt, M. R.; Hruby, V. J.; Polt, R. (2001) Solid-Phase Synthesis of 0-Linked Glycopeptide Analogues of Enkephalin. J. Org. Chem. 66, 2327-2342.
28. Lefever, M. R.; Szabo, L. Z.; Anglin, B.; Hogan, J.; Cooney, L.; Polt, R. (2012) Glycosylation of α-amino acids by sugar acetate donors with $InBr_3$. Minimally competent Lewis acids. Carbohydr. Research 351, 121-125.
29. Li, Y.; Lefever, M. R.; Muthu, D.; Bidlack, J. M.; Bilsky, E. J.; Polt, R. (2012) Opioid glycopeptide analgesics derived from endogenous enkephalins and endorphins. Future Med. Chem. 4, 205-226.
30. Robberecht, P.; Gourlet, P.; Deneef, P.; et al. (1992) Structural requirements for the occupancy of pituitary adenylate-cyclase-activating-peptide (PACAP) receptors and adenylate cyclase activation in human neuroblastoma NB-OK-1 cell membranes. Discovery of $PACAP_{6-38}$ as a potent antagonist. Eur. J. Biochem. 207, 239-246.
31. Gourlet et al. 1995
32. Zhang, C.; Miller, W.; Valenzano, K. J.; Kyle, D. J. J. Med. Chem. 2002, 45, 5280-5286.
33. Banks, W. A. Delivery of Peptides to the Brain: Emphasis on Therapeutic Development. Peptide Science 90, 589-594 (2008).
34. Banks, W. A.; Kastin, A. J.; Komaki, G.; Arimura, A. Passage of pituitary adenylate cyclase activating polypeptide 1-27 and pituitary adenylate cyclase activating polypeptide-38 across the blood-brain barrier. J. Pharm. Exp. Therap. 267, 690-696 (1993).
35. Dogrukol-Ak, D.; Tore, F.; Tuncel, N. Passage of VIP/PACAP/secretin family across the blood-brain barrier: therapeutic effects. Curr. Pharm. Des. 10, 1325-1340 (2004).
36. Yue X., Falk T., Zuniga L. A., Szabo L., Porreca F., Polt R., Sherman S. J. Effects of the novel glycopeptide opioid agonist MMP-2200 in preclinical models of Parkinson's disease. Brain Research, 1413: 72-83 (2011).

37. Mabrouk, O. S.; Falk, T.; Sherman, S. J.; Kennedy, R. T.; Polt, R. CNS penetration of the opioid glycopeptide MMP-2200: A microdialysis study. *Neurosci. Lett.* 531, 99-103 (2012).
38. Egleton, R. D.; Mitchell, S. A.; Huber, J. D.; Palian, M. M.; Polt, R.; Davis, T. P. Improved blood-brain barrier penetration and enhanced analgesia of an opioid peptide by glycosylation. *J Pharm. Exp. Ther.* 299, 967-972 (2001).
39. Li, Y.; Lefever, M. R.; Muthu, D.; Bidlack, J. M.; Bilsky, E. J.; Polt, R. Opioid glycopeptide analgesics derived from endogenous enkephalins and endorphins. *Future Med. Chem.* 4, 205-226 (2012).
40. Dejda, A.; Sokowska, P.; Nowak, J. Z. Neuroprotective potential of three neuropeptides PACAP, VIP and PHI. *Pharmcol. Reports* 57, 307-320 (2005).
41. Waschek J. A. VIP and PACAP: neuropeptide modulators of CNS inflammation, injury, and repair. *British Journal of Pharmacology* 169 512-523 (2013).
42. Watson M. B., Nobuta H., Abad C., Lee S. K., Bala N., Zhu C., Richter F., Chesselet M. F., Waschek J. A. PACAP deficiency sensitizes nigrostriatal dopaminergic neurons to paraquat-induced damage and modulates central and peripheral inflammatory activation in mice. *Neuroscience* 240, 277-286 (2013).
43. Ringer, C.; Büning, L. S.; Schäfer, M. K. H.; Eiden, L. E.; Weihe, E.; Schütz, B. PACAP signaling exerts opposing effects on neuroprotection and neuroinflammation during disease progression in the SOD1 (G93A) mouse model of amyotrophic lateral sclerosis. *Neurobiol. Disease* 54, 32-42 (2013).

The invention claimed is:

1. A pharmaceutical composition comprising a glycosylated pleiotropic peptide pituitary adenylate cyclase-activating polypeptide (PACAP) in a pharmaceutically acceptable carrier, wherein leucine 1 of said glycosylated PACAP is replaced with serine, and wherein said serine is glycosylated, and wherein said glycosylated PACAP comprises the amino acid sequence of SEQ ID NO:4.

2. The pharmaceutical composition of claim 1, wherein the glycosylated PACAP comprises the amino acid sequence of SEQ ID NO:4 and is a 27-amino acid peptide.

3. The pharmaceutical composition of claim 1, wherein the glycosylated PACAP comprises the amino acid sequence of SEQ ID NO:4 and is a 38-amino acid peptide.

4. The pharmaceutical composition of claim 1, wherein said PACAP is glycosylated with a monosaccharide or disaccharide.

5. A glycosylated pleiotropic peptide pituitary adenylate cyclase-activating polypeptide (PACAP), wherein the PACAP comprises the amino acid sequence of SEQ ID NO:3, and wherein leucine 1 of the PACAP is replaced with serine, and wherein said serine is glycosylated.

6. The glycosylated PACAP of claim 5, wherein the PACAP comprises the amino acid sequence of SEQ ID NO:4 and is a 27-amino acid peptide.

7. The glycosylated PACAP of claim 5, wherein said PACAP is glycosylated with a monosaccharide or a disaccharide.

8. The glycosylated PACAP of claim 5, wherein said PACAP is glycosylated with a saccharide selected from the group consisting of ß-D-glucose, ß-maltose, ß-lactose, ß-melibiose, ß-maltotriose, sucrose, trehalose, saccharose, maltose, cellobiose, gentibiose, isomaltose, primeveose, galactose, xylose, mannose, manosaminic acid, fucose, GalNAc, GlcNAc, idose, iduronic acid, glucuronic acid and sialic acid.

9. A method for promoting neuronal survival and neurite outgrowth in an individual with a neurodegenerative disease comprising administering to the individual in need thereof, a therapeutically effective amount of a composition of claim 1; wherein the neurodegenerative disease is selected from the group consisting of amyotrophic lateral sclerosis (ALS), Parkinson's Disease (PD), traumatic brain injury, stroke and dementia.

10. The method of claim 9, wherein the method comprises the administration of an effective amount of the glycosylated PACAP-of claim 2.

11. The method of claim 9, wherein said method comprises the administration of an effective amount of the glycosylated PACAP-of claim 3.

12. The method of claim 9, wherein the therapeutically effective amount comprises a unit dose amount of between 0.1 and 10 milligrams per kilo.

13. The method of claim 12, wherein the dose is administered once a day.

14. The method of claim 12, wherein the dose is administered twice a day.

* * * * *

```
                        SEQUENCE LISTING

<160> NUMBER OF SEQ ID NOS: 11

<210> SEQ ID NO 1
<211> LENGTH: 38
<212> TYPE: PRT
<213> ORGANISM: Homo sapiens

<400> SEQUENCE: 1

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 2
<211> LENGTH: 38
<212> TYPE: PRT
<213> ORGANISM: Homo sapiens
<220> FEATURE:
<221> NAME/KEY: MISC_FEATURE
<222> LOCATION: (38)..(38)
<223> OTHER INFORMATION: Terminal -OH group replaced with -NH2 group

<400> SEQUENCE: 2

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 3
<211> LENGTH: 27
<212> TYPE: PRT
<213> ORGANISM: Homo sapiens
<220> FEATURE:
<221> NAME/KEY: MISC_FEATURE
<222> LOCATION: (27)..(27)
<223> OTHER INFORMATION: Terminal -OH group replaced with -NH2 group

<400> SEQUENCE: 3

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25
```

<210> SEQ ID NO 4
<211> LENGTH: 27
<212> TYPE: PRT
<213> ORGANISM: Artificial Sequence
<220> FEATURE:
<223> OTHER INFORMATION: PACAP1-27-S-G
<220> FEATURE:
<221> NAME/KEY: CARBOHYD
<222> LOCATION: (27)..(27)
<223> OTHER INFORMATION: OH group of serine attached to glucose
<220> FEATURE:
<221> NAME/KEY: MISC_FEATURE
<222> LOCATION: (27)..(27)
<223> OTHER INFORMATION: Terminal -OH group replaced with -NH2 group

<400> SEQUENCE: 4

His Ser Asp Gly Ile Phe Thr Asp Ser Tyr Ser Arg Tyr Arg Lys Gln
1               5                   10                  15

Met Ala Val Lys Lys Tyr Leu Ala Ala Val Ser
            20                  25

<210> SEQ ID NO 5
<211> LENGTH: 22
<212> TYPE: PRT
<213> ORGANISM: Artificial Sequence
<220> FEATURE:
<223> OTHER INFORMATION: PACAP6-27
<220> FEATURE:
<221> NAME/KEY: MISC_FEATURE
<222> LOCATION: (22)..(22)
<223> OTHER INFORMATION: terminal -OH group replaced with -NH2 group

<400> SEQUENCE: 5

Phe Thr Asp Ser Tyr Ser Arg Tyr Arg Lys Gln Met Ala Val Lys Lys
1               5                   10                  15

Tyr Leu Ala Ala Val Leu
            20

<210> SEQ ID NO 6
<211> LENGTH: 33
<212> TYPE: PRT
<213> ORGANISM: Artificial Sequence
<220> FEATURE:
<223> OTHER INFORMATION: PACAP6-38
<220> FEATURE:
<221> NAME/KEY: misc_feature
<222> LOCATION: (33)..(33)
<223> OTHER INFORMATION: Terminal -OH group replaced with -NH2 group

<400> SEQUENCE: 6

Phe Thr Asp Ser Tyr Ser Arg Tyr Arg Lys Gln Met Ala Val Lys Lys
1               5                   10                  15

Tyr Leu Ala Ala Val Leu Gly Lys Arg Tyr Lys Gln Arg Val Lys Asn
            20                  25                  30

Tyr

<210> SEQ ID NO 7
<211> LENGTH: 22
<212> TYPE: PRT
<213> ORGANISM: Artificial Sequence
<220> FEATURE:
<223> OTHER INFORMATION: PACAP6-27-S-G
<220> FEATURE:
<221> NAME/KEY: misc_feature
<222> LOCATION: (22)..(22)
<223> OTHER INFORMATION: Terminal -OH group replaced with -NH2 group
<220> FEATURE:
<221> NAME/KEY: misc_feature -continued

```
<222> LOCATION: (22)..(22)
<223> OTHER INFORMATION: Hydroxyl group of serine attached to glucose

<400> SEQUENCE: 7

Phe Thr Asp Ser Tyr Ser Arg Tyr Arg Lys Gln Met Ala Val Lys Lys
1               5                   10                  15

Tyr Leu Ala Ala Val Ser
            20

<210> SEQ ID NO 8
<211> LENGTH: 22
<212> TYPE: PRT
<213> ORGANISM: Artificial Sequence
<220> FEATURE:
<223> OTHER INFORMATION: PACAP6-27-S-L
<220> FEATURE:
<221> NAME/KEY: MISC_FEATURE
<222> LOCATION: (22)..(22)
<223> OTHER INFORMATION: Terminal -OH group replaced with -NH2 group
<220> FEATURE:
<221> NAME/KEY: CARBOHYD
<222> LOCATION: (22)..(22)
<223> OTHER INFORMATION: Hydroxyl group of serine attached to D-glucose

<400> SEQUENCE: 8

Phe Thr Asp Ser Tyr Ser Arg Tyr Arg Lys Gln Met Ala Val Lys Lys
1               5                   10                  15

Tyr Leu Ala Ala Val Ser
            20

<210> SEQ ID NO 9
<211> LENGTH: 22
<212> TYPE: PRT
<213> ORGANISM: Artificial Sequence
<220> FEATURE:
<223> OTHER INFORMATION: PACAP6-27-Alt
<220> FEATURE:
<221> NAME/KEY: MISC_FEATURE
<222> LOCATION: (22)..(22)
<223> OTHER INFORMATION: Terminal -OH group replaced with -NH2 group

<400> SEQUENCE: 9

Phe Thr Asp Ser Tyr Ser Arg Tyr Arg Arg Gln Leu Ala Val Arg Arg
1               5                   10                  15

Tyr Leu Ala Ala Val Leu
            20

<210> SEQ ID NO 10
<211> LENGTH: 22
<212> TYPE: PRT
<213> ORGANISM: Artificial Sequence
<220> FEATURE:
<223> OTHER INFORMATION: PACAP6-27-S-G-Alt
<220> FEATURE:
<221> NAME/KEY: MISC_FEATURE
<222> LOCATION: (22)..(22)
<223> OTHER INFORMATION: Terminal -OH group replaced with -NH2 group
<220> FEATURE:
<221> NAME/KEY: CARBOHYD
<222> LOCATION: (22)..(22)
<223> OTHER INFORMATION: Hydroxyl group of Serine attached to D-glucose

<400> SEQUENCE: 10

Phe Thr Asp Ser Tyr Ser Arg Tyr Arg Arg Gln Leu Ala Val Arg Arg
1               5                   10                  15

Tyr Leu Ala Ala Val Ser
            20
```

```
<210> SEQ ID NO 11
<211> LENGTH: 22
<212> TYPE: PRT
<213> ORGANISM: Artificial Sequence
<220> FEATURE:
<223> OTHER INFORMATION: PACAP6-27-S-L-Alt
<220> FEATURE:
<221> NAME/KEY: MISC_FEATURE
<222> LOCATION: (22)..(22)
<223> OTHER INFORMATION: Terminal -OH group replaced with -NH2 group
<220> FEATURE:
<221> NAME/KEY: CARBOHYD
<222> LOCATION: (22)..(22)
<223> OTHER INFORMATION: Hydroxyl group of Serine attached to D-lactose

<400> SEQUENCE: 11

Phe Thr Asp Ser Tyr Ser Arg Tyr Arg Arg Gln Leu Ala Val Arg Arg
1               5                   10                  15

Tyr Leu Ala Ala Val Ser
            20
```